(12) United States Patent
Hersh et al.

(10) Patent No.: US 9,044,503 B2
(45) Date of Patent: Jun. 2, 2015

(54) AMYLOID PEPTIDE INACTIVATING ENZYME TO TREAT ALZHEIMER'S DISEASE PERIPHERALLY

(75) Inventors: Louis B. Hersh, Lexington, KY (US); Hanjun Guan, Lexington, KY (US)

(73) Assignee: UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 1051 days.

(21) Appl. No.: 11/661,274

(22) PCT Filed: Aug. 26, 2005

(86) PCT No.: PCT/US2005/030396
§ 371 (c)(1),
(2), (4) Date: Aug. 28, 2008

(87) PCT Pub. No.: WO2006/026426
PCT Pub. Date: Mar. 9, 2006

(65) Prior Publication Data
US 2008/0317732 A1      Dec. 25, 2008

Related U.S. Application Data

(60) Provisional application No. 60/604,700, filed on Aug. 27, 2004.

(51) Int. Cl.
| | | |
|---|---|---|
| *A61K 38/48* | (2006.01) | |
| *C12N 5/00* | (2006.01) | |
| *A61K 48/00* | (2006.01) | |
| *C12N 9/64* | (2006.01) | |
| *C12N 15/86* | (2006.01) | |
| *A61K 38/00* | (2006.01) | |

(52) U.S. Cl.
CPC .............. *A61K 48/00* (2013.01); *C12N 9/6494* (2013.01); *C12N 15/86* (2013.01); *C12N 2740/15043* (2013.01); *C12N 2830/008* (2013.01); *C12N 2830/48* (2013.01); *C12Y 304/24011* (2013.01); *A61K 38/00* (2013.01)

(58) Field of Classification Search
CPC ..... A61K 48/00; A61K 38/00; C12N 9/6494; C12N 15/86; C12N 2740/15043; C12N 2830/008; C12N 2830/48; C12Y 304/24011
USPC .............................. 424/94.63; 435/325
See application file for complete search history.

(56) References Cited

U.S. PATENT DOCUMENTS

| | | | |
|---|---|---|---|
| 4,897,389 A | 1/1990 | Aroonsakul | |
| 5,554,601 A | 9/1996 | Simpkins et al. | |
| 5,624,894 A | 4/1997 | Bodor | |
| 5,952,346 A | 9/1999 | Heitsch et al. | |
| 6,333,317 B1 | 12/2001 | Lee et al. | |
| 2002/0091072 A1* | 7/2002 | Eckman et al. | 514/1 |
| 2003/0003087 A1* | 1/2003 | Eglitis et al. | 424/93.21 |
| 2003/0083277 A1* | 5/2003 | Hersh | 514/44 |
| 2004/0038302 A1 | 2/2004 | Nitsch et al. | |
| 2006/0018889 A1* | 1/2006 | Li et al. | 424/93.21 |

FOREIGN PATENT DOCUMENTS

| | | |
|---|---|---|
| WO | WO 02/22794 | 3/2002 |
| WO | WO 02/25279 | 3/2002 |
| WO | WO 02/087552 | 11/2002 |

OTHER PUBLICATIONS

Hanawa et al Human Gene Therapy, 2002, 13, 2007-2016.*
Matsuoka et al The Journal of Neuroscience, 2003, 23(1), 29-33.*
Marr et al Journal of Neuroscience, Mar. 15, 2003.23(6):1992-1996.*
Liu et al. Molecular Therapy. 2009; 17(8): 1381-1386.*
Walker The Journal of Neuroscience, 2013, 33(6):2457-2464.*
Verma and Somia (1997) Nature 389:239-242 and.*
Verma Annu. Rev. Biochem. 2005. 74:711-38.*
Sata et al Nature Medicine, 2002, 403-409.*
Marr et al Journal of Molecular Neuroscience, 2004, 5-11.*
Foust et al 2009, Nat Biotechnol 27: 59-65.*
Zlokovic et al (Journal of Neurochemistry, 2004, 89(4), 807-811.*
Carson JA, Turner AJ. J Neurochem. Apr. 2002;81(1):1-8. *Beta-amyloid catabolism: roles for neprilysin (NEP) and other metallopeptidases?*
Chesneau V, Vekrellis K, Rosner MR, Selkoe DJ. Biochem J. Oct. 15, 2000;351 Pt 2:509-16. *Purified recombinant insulin-degrading enzyme degrades amyloid beta-protein but does not promote its oligomerization.*
Eckman EA, Watson M, Marlow L, Sambamurtl K, Eckman CB. J Biol Chem. Jan. 24, 2003;278(4):2081-4. Epub Dec. 2, 2002. *Alzheimer's disease beta-amyloid peptide is increased in mice deficient in endothelin-converting enzyme.*
Hama E, Shirotani K, Masumoto H, Sekine-Aizawa Y, Alzawa H, Saido TC. J Biochem (Tokyo). Dec. 2001;130(6):721-6. *Clearance of extracellular and cell-associated amyloid beta peptide through viral expression of neprilysin in primary neurons.*

(Continued)

*Primary Examiner* — Anoop Singh
(74) *Attorney, Agent, or Firm* — McDermott Will & Emery LLP

(57) ABSTRACT

Methods for treatment and/or prevention of Alzheimer's disease comprising inactivating peripheral AP in serum to a reduce A(3 in the brain. Methods comprise expression of amyloid peptide inactivating enzyme on bone marrow cells; and coupling of amyloid peptide inactivating enzyme to hematopoietic cells.

5 Claims, 15 Drawing Sheets

(56) References Cited

OTHER PUBLICATIONS

Haouas H, Morello D, Lavenu A, Billard M, Jasmin C, Boucheix C. Biochem Biophys Res Commun. Feb. 27, 1995;207(3):933-42. *Characterization of the 5' region of the CD10/neutral endopeptidase 24.11 gene.*
Henderson VW, Paganini-Hill A, Miller BL, Eible RJ, Reyes PF, Shoupe D, McCleary CA, Klein RA, Hake AM, Farlow MR. Neurology. Jan. 25, 2000;54(2):295-301. *Estrogen for Alzheimer's disease in women: randomized, double-blind, placebo-controlled trial.*
Howell S, Nalbantoglu J, Crine P. Peptides. 1995;16(4):647-52. *Neutral endopeptidase can hydrolyze beta-amylold(1-40) but shows no effect on beta-amyloid precursor protein metabolism.*
Ishimaru F, Mari B, Shipp MA. Blood. Jun. 1, 1997;89(11):4136-45. *The type 2 CD10/neutral endopeptidase 24.11 promoter: functional characterization and tissue-specific regulation by CBF/NF-Y isoforms.*
Iwata N, Tsubuki S, Takaki Y, Watanabe K, Sekiguchi M, Hosoki E, Kawashima-Morishima M, Lee HJ, Hama E, Sekine-Aizawa Y, Saido TC. Nat Med. Feb. 2000;6(2):143-50. *Identification of the major Abeta1-42-degrading catabolic pathway in brain parenchyma: suppression leads to biochemical and pathological deposition.*
Iwata N, Tsubuki S, Takaki Y, Shirotani K, Lu B, Gerard NP, Gerard C, Hama E, Lee HJ, Saido TC. Science. May 25, 2001;292(5521):1550-2. *Metabolic regulation of brain Abeta by neprilysin.*
Kurochkin IV. Trends Biochem Sci. Jul. 2001;26(7):421-5. *Insulin-degrading enzyme: embarking on amyloid destruction.*
Li C, Hersh LB. Arch Biochem Biophys. Oct. 1, 1998;358(1):189-95. *Characterization of the promoter region of the rat neprilysin gene.*
Li C, Booze RM, Hersh LB. J Biol Chem. Mar. 17, 1995;270(11):5723-8. *Tissue-specific expression of rat neutral endopeptidase (neprilysin) mRNAs.*
Li C, Guojin Chen, Norma P. Gerard, Craig Gerard, Carmen R Bozic, Louis B. Hersh "Comparison of the structure and expression of the human rat neprilysin (endopeptidase 24.11)- encoding genes." Gene. 164 (1995) pp. 363-366.
Marr RA, Rockenstein E, Mukherjee A, Kindy MS, Hersh LB, Gage FH, Verma IM, Masliah E. J Neurosci. Mar. 15, 2003;23(6):1992-6. *Neprilysin gene transfer reduces human amyloid pathology in transgenic mice.*
McDermott JR, Gibson AM. Neurochem Res. Jan. 1997;22(1):49-56. *Degradation of Alzheimer's beta-amyloid protein by human and rat brain peptidases: involvement of insulin-degrading enzyme.*
Miller BC, Eckman EA, Sambamurti K, Dobbs N, Chow KM, Eckman CB, Hersh LB, Thiele DL. Proc Natl Acad Sci U S A. May 13, 2003;100(10):6221-6. Epub May 5, 2003. *Amyloid-beta peptide levels in brain are inversely correlated with insulysin activity levels in vivo.*
Mohajeri MH, Woilmer MA, Nitsch RM. J Biol Chem. Sep. 20, 2002;277(38):35460-5. Epub Jul. 8, 2002. *Abeta 42-induced increase in neprilysin is associated with prevention of amyloid plaque formation in vivo.*
Perez A, Morelli L, Cresto JC, Castano EM. Neurochem Res. Feb. 2000;25(2):247-55. *Degradation of soluble amyloid beta-peptides 1-40, 1-42, and the Dutch variant 1-40Q by insulin degrading enzyme from Alzheimer disease and control brains.*
Petanceska SS, Nagy V, Frail D, Gandy S. Exp Gerontol. Dec. 2000;35(9-10):1317-25. *Ovariectomy and 17beta-estradiol modulate the levels of Alzheimer's amyloid beta peptides in brain.*
Pinto FM, Armesto CP, Magraner J, Trujillo M, Martin JD, Candenas ML. Endocrinology. Jun. 1999;140(6):2526-32. *Tachykinin receptor and neutral endopeptidase gene expression in the rat uterus: characterization and regulation in response to ovarian steroid treatment.*
Qiu WQ, Walsh DM, Ye Z, Vekrellis K, Zhang J, Podlisny MB, Rosner MR, Safavi A, Hersh LB, Selkoe DJ. J Biol Chem. Dec. 4, 1998;273(49):32730-8. *Insulin-degrading enzyme regulates extracellular levels of amyloid beta-protein by degradation.*
Shen R, Sumitomo M, Dal J, Hardy DO, Navarro D, Usmani B, Papandreou CN, Hersh LB, Shipp MA, Freedman LP, Nanus DM. Mol Cell Endocrinol. Dec. 22, 2000;170(1-2):131-42. *Identification and characterization of two androgen response regions in the human neutral endopeptidase gene.*
Shirotani K, Tsubukl S, Iwata N, Takaki Y, Harigaya W, Maruyama K, Kiryu-Seo S, Kiyama H, Iwata H, Tomita T, Iwatsubo T, Saldo TC. J Biol Chem. Jun. 15, 2001;276(24):21895-901. Epub Mar. 6, 2001. *Neprilysin degrades both amyloid beta peptides 1-40 and 1-42 most rapidly and efficiently among thiorphan- and phosphoramidon-sensitive endopeptidases.*
Song ES, Mukherjee A, Juliano MA, Pyrek JS, Goodman JP Jr, Juliano L, Hersh LB. J Biol Chem. Jan. 12, 2001;276(2):1152-5. *Analysis of the subsite specificity of rat insulysin using fluorogenic peptide substrates.* Tharaux PL, Stefanski A, Ledoux S, Soleilhac JM, Ardaillou R, Dussaule JC. Am J Physiol. Jun. 1997;272(6 Pt 1):C1836-43. *EGF and TGF-beta regulate neutral endopeptidase expression in renal vascular smooth muscle cells.*
Tharaux PL, Stefanski A, Ledoux S, Soleilhac JM, Ardaillou R, Dussaule JC. Am J Physiol. Jun. 1997;272(6 Pt 1):C1836-43. *EGF and TGF-beta regulate neutral endopeptidase expression in renal vascular smooth muscle cells.*
Vekrellis K, Ye Z, Qiu WQ, Walsh D, Hartley D, Chesneau V, Rosner MR, Seikoe DJ. J Neurosci. Mar. 1, 2000;20(5):1657-65. *Neurons regulate extracellular levels of amyloid beta-protein via proteolysis by insulin-degrading enzyme.*
Koji Yasojima, Haruhiko Akiyama, Edith G. McGeer, and Patrick L. McGeer, "Reduced Neprilysin in High Plaque Areas of Alzheimer Brains; a Possible Relationship to Deficient Degradation of β-Amyloid Peptide", Neuroscience Letters 297, (2001) pp. 97-100.
Atish Mukherjee, Eun-Suk Song, Muthoni Kihiko-Ehmann, Jack P. Goodman Jr, Jan St. Pyrek, Steven Estus, and Louis B. Hersh, "Insulysin Hydrolyzes Amyloid β Peptides to Products that are Neither Neurotoxic Nor Deposit on Amyloid Plaques", The Journal of Neuroscience, Dec. 1, 2000, 20(23) pp. 8745-8749.
Yoshie Takaki, Nobuhisa Iwata, Satoshi Tsubuki, Sayuri Taniguchi, Satoshi Toyoshima, Bao Lu, Norma P. Gerard, Craig Gerard, Hahn-Jun Lee, Keiro Shirotani, and Takaomi C. Saido, "Biochemical Identification of the Neutral Endopeptidase Family Member Responsible for the Catabolism of Amyloid β Peptide in the Brain," The Japanese Biochemical Society vol. 128, (2000) pp. 897-902.
Igor V. Kurochkin, Sataro Goto, "Alzheimer's β-Amyloid Peptide Specifically Interacts With and is Degraded by Insulin Degrading Enzyme", FEBS Letters 345 (1994) 33-37.
Fukami S, Watanabe K, Iwata N, Haraoka J, Lu B, Gerard NP, Gerard C, Fraser P, Westaway D, St. George-Hyslop P, Saido TC. "A β-Degrading Endopeptidase, Neprilysin, in Mouse Brain; Synaptic and Axonal Localization Inversely Correlating With a β-Pathology." Neurosci Res. May 2002; 43(1):39-56.
Hauss-Wegrzyniak B, Wenk GL. "β-Amyloid Deposition in the Brains of Rats Chronically Infused With Thiorphan or Lipopolysaccharide: The Role of Ascorbic Acid in the Vehicle" Neurosci Lett. Apr. 5, 2002;322(2):75-8.
Oda M, Morino H, Maruyama H, Terasawa H, Izumi Y, Torii T, Sasaki K, Nakamura S, Kawakami H. "Dinucleotide Repeat Polymorphins in the Neprilysin Gene are not Associated With Sporadic Alzheimer's Disease." Neurosci Lett. Mar. 1, 2002;320(12):105-7.
Abraham R, Myers A, Wavrant-Devrieze F, Hamshere ML, Thomas HV, Marshall H, Compton D, Spurlock G, Turic D, Hoogendoorn B, Kwon JM, Petersen RC, Tangalos E, Norton J, Morris JC, Bullock R, Liolitsa D, Lovestone S, Hardy J, Goate A, O'Donovan M, Williams J, Owen MJ, Jones L. "Substantial Linkage Disequilibrium Across the Insulin-Degrading Enzyme Locus But no Association With Late-Onset Alzheimer's Disease" Hum Genet. Dec. 2001; 109(6):646-52.
Selkoe DJ "Clearing the Brain's Amyloid Cobwebs" Neuron. Oct. 25, 2001;32(2):177-80.
Fricke B, Betz R, Friebe S, "A Periplasmic Insulin-Cleaving Proteinase (ICP) From *Acinetobacter calcoaceticus* Sharing Properties With Protease II From *Escherichia coli* and IDE From Eukaryotes" Chemical Abstracts, 1995;123:77933X.
Espinosa R III, Lemons RS, Perlman RK, Kuo WL, Rosner MR, Lebeau MM "Localization of the Gene Encoding Insulin-Degrading Enzyme to Human Chromosome 10, Bands Q23-Q25" J-Biochem Genetics, 1992; 116:77617C.

(56) References Cited

OTHER PUBLICATIONS

Sakamoto T, "Establishment of Radioimmunoassay for Human Crythrocyte Insulin-Degrading Enzyme (IDE) and its Clinical Application" 7-Enzymes, 1989; 111:92605N.

Sodeyama N, Mizusawa H, Yamada M, Itoh Y, Otomo E, Matsushita M, "Lack of Association of of Neprilysin Polymorphism With Alzheimer's Disease and Alzheimer's Disease-Type Neuropathological Changes" J. Neurol Neurosurg Psychiatry 2001; 71:817-824.

Nitsch et al. "Upregulation of Neprilysin Prevents Amyloid Plaque Formation in SWAPP Transgenic Mice", Soc. for Neuroscience Abstracts., Oct. 2001, vol. 27, No. pp. 926.

Tanzi et al. "Clearance of Alzheimer's AB Peptide: The Many Roads to Perdition", Neuron Sep. 2004, vol. 43, No. 5, pp. 605-608.

Clark et al., 1993, Arch, Neurol., 50, pp. 1164-1172.

Orkin and Molulsky (1995) Report and recommendations of the panel to assess the NIH investment in research on gene therapy, pp. 1-40.

Ross et al. (1996) Gene therapy in the United States: A five year status report. Human Gene Therapy 7: 1781-1790.

Rubanyi (2001) The future of human gene therapy. Mol. Aspects Med. 22: 113-142.

Verma et al. (1997) Gene therapy—promises, problems and prospects. Nature 389; 239-242.

Crystal (1995) Transfer of genes to humans: Early lessons and obstacles to success. Science 270: 404-410.

Deonarain (1998) Ligand-Targeted receptor-mediated vectors for gene delivery. Exp. Opin. Ther. Patents 8(1): 53-69.

Friedmann (1997) Overcoming the obstacles to gene therapy. Scientific American, Jun. 1997, pp. 97-101.

Miller et al. (1995) Targeted vectors for gene therapy. FASEB. J. 9: 190-199.

Liu et al., Expression of Neprilysin in Skeletal Muscle Reduces Amyloid Burden in a Transgenic Mouse Model of Alzheimer Disease, Molecular Therapy, vol. 17, No. 8, 1381-1386, Aug. 2009.

Bard, et all, Perpipherally Administered Antibodies Against Amyloid b-Peptide Enter the Central Nervous System and Reduct Pathology in a Mouse Model of Alzheimer Disease, Nature Medicine, vol. 6, No. 8, Aug. 2000.

Guan, et al. Peripherally Expresses Neprilysin Reduces Brain Amyloid Burden: A Novelapproach for Treating Alzheimer's Disease, Journal of Neuroscience Research 87:1462-1473 (2009).

Carare et al., "Immune complex formation impairs the elimination of solutes from the brain: implications for immunotherapy in Alzheimer's disease," Acta Neuropathologica Communications 2013, 1:48.

"Sustained peripheral depletion of amyloid-$\beta$ with a novel form of neprilysin does not affect central levels of amyloid-$\beta$" by Simon J. Henderson et al., Brain: A Journal of Neurology, p. 1-12, Nov. 20, 2013.

"Enhanced Proteolytic Clearance of Plasma A$\beta$ by Peripherally Administered Neprilysin Does Not Result in Reduced Levels of Brain A$\beta$ in Mice", by John R. Walker et al., The Journal of Neuroscience, p. 2457-2464, Feb. 6, 2013.

"Peripherally expressed neprilysin reduces brain amloid burden: A novel approach for treating Alzheimer's disease", by Hanjun Guan et al., J Neurosci Res., p. 1462-1473, May 1, 2009.

\* cited by examiner

A  B

A B C

A  B  C

Control  NEP  NEPx

Figure 6

Peripheral (blood) NEP introduced by bone marrow transplantation reduces brain Aβ peptide levels in APP transgenic mice. Amyloid β peptide levels were determined by RIA.

|  | Active NEP | Inactive NEP |
|---|---|---|
| Aβ40 (ng/ml) | 279.58 ± 56.12 (0.52) | 533.00 ± 11.46* (1.0) |
| Aβ42 (ng/ml) | 919.58 ± 48.85 (0.70) | 1312.50 ± 30.41* (1.0) |

The levels of Aβ peptides in the mice treated with active NEP are statistically lower than those of the mice treated with inactive NEP. * $P<0.01$ Peripheral (blood) NEP introduced by bone marrow transplantation reduces amyloid peptide deposition in the brain. Amyloid deposits were visualized in APP transgenic mouse brains by thioflavin-S staining.

Inactive NEP     Active NEP-BMT

Figure 10.

|  | Reaction Time (hours) | ▢▢▢▢▢▢▢y (Arbitrary units) | % Activity Remaining |
|---|---|---|---|
|  | 0 | 285 |  |
| untreated | 1 | 302 | 100 |
|  | 2 | 278 | 98 |
|  | 4 | 238 | 95 |
|  |  |  |  |
| biotinylated | 1 | 242 | 85 |
|  | 2 | 210 | 74 |
|  | 4 | 169 | 59 |

FACS analysis of red blood cells biotinylated with biotin-N-hydroxysuccinimde.

Biotinylated-NEP binds to streptavidin-conjugated biotinylated-red blood cells.

Figure 13

Secreted NEP modified to contain a C-terminal red blood cell binding peptide.

| SS | Neprilysin Ectodomain | red blood cell binding peptide |

Secreted NEP unmodied.

| SS | Neprilysin Ectodomain |

SS: Pre-Pro Trypsin secretory signal.
Red blood cell binding peptide: NNSAFNNNLCSKNAKGLNLN.

Figure 15.

NEP modified to contain a C- terminal single chain antibody directed at a red blood cell epitope.

$V_L$ and $V_H$ represent the variable heavy and light chain domains of the single chain antibody

AMYLOID PEPTIDE INACTIVATING ENZYME TO TREAT ALZHEIMER'S DISEASE PERIPHERALLY

RELATED APPLICATIONS

This application is a national phase of PCT/US2005/030396 which claims priority from U.S. Provisional Application No. 60/604,700 filed Aug. 27, 2004, the disclosures of which Applications are incorporated by reference herein. The benefit of the filing and priority dates of the International and U.S. Applications is respectfully requested.

GOVERNMENT INTEREST IN THE INVENTION

This invention was made with Government support under four grants: (1) grant no. UKRF#465181 awarded by the Alzheimer's Association, (2) grant no. DA02243 awarded by the National Institute on Drug Abuse, (3) grant no. AG19323 awarded by the National Institute on Aging, and (4) grant no. AG024899 also awarded by the National Institute on Aging. The Government has certain rights in this invention.

FIELD OF THE INVENTION

The present invention relates to methods of and transduced stem cells and modified peptidase for preventing amyloid peptide (A$\beta$) accumulation, and plaque formation in the brain by raising amyloid peptide inactivating enzyme activity in the periphery. The present invention also relates to methods of lowering plasma A$\beta$ levels as a way to lower brain A$\beta$ using expression of amyloid peptide inactivating enzymes, like neprilysin, on hematopoietic cells. The present invention also relates to a method of treating and/or preventing Alzheimer's disease.

BACKGROUND OF THE INVENTION

The incidence of Alzheimer's disease (AD) is estimated to currently affect up to 4 million Americans and this number will certainly increase as our population continues to age. Approximately 3% of the population between ages 65 to 74 suffer from AD, and this value increases with increasing age. Since AD patients generally live 8 to 10 years after the disease is diagnosed, the financial burden AD imposes on our economy is estimated to exceed $100 billion and will continue to increase. Although there are a number of acetylcholinesterase inhibitors as approved drugs that can improve the symptoms of AD patients over the short term, no current therapy can retard disease progression. It is widely accepted that the oligomerization and subsequent deposition of amyloid $\beta$ peptides (A$\beta$) is a major factor in AD. Thus considerable effort has been expended in the development of drugs that can selectively inhibit the $\beta$ and $\gamma$ secretases responsible for A$\beta$ formation. To date no such drugs have reached the marketplace.

In recent years attention has been given to the peptidases that are involved in amyloid peptide (e.g., A$\beta$) clearance, such as neprilysin and insulysin. It has been shown that inhibition or deletion of these peptidases in rodent models leads to elevated A$\beta$, and that introduction of these peptidases into the brain of transgenic mice expressing human amyloid precursor protein (hAPP) can lead to a reduction in A$\beta$ levels (Leissring M A, et al. (2003). *Enhanced proteolysis of beta-amyloid in APP transgenic mice prevents plaque formation, secondary pathology, and a premature death*. Neuron 40, 1087-1093). In addition expression of neprilysin in the brain can reduce the number of preformed amyloid plaques (Marr, R. A. et al. (2003) *Neprilysin gene transfer reduces amyloid pathology in mouse models of Alzheimer's disease*. J. Neurosci. 23:1992-1996). This is the first report that shows that neprilysin can actually be used to "dissolve" preformed plaques. Since neprilysin does not degrade aggregated A$\beta$, this demonstrates that the aggregated A$\beta$ must be in a dynamic equilibrium with free A$\beta$ or small A$\beta$ oligomers. We have also conducted preliminary experiments designed to test the effect of neprilysin expression in the brain of an hAPP mouse model as a way to degrade A$\beta$ and prevent amyloid deposits from forming. As shown in FIG. 3, we found that using the lentivirus-neprilysin construct to express neprilysin in the hippocampus of the J20 human hAPP transgenic mouse model of AD, virtually eliminated amyloid deposits in the 9-month old mouse. (Id.). In the lentivirus-NEP treated brain (FIG. 3B, right) there is a small amount of diffuse light staining material, indicative of amyloid peptide, as compared to the control lentivirus-GFP (FIG. 3A, right). (Id.).

More recently interest has emerged in targeting the clearance of A$\beta$ peptides as a therapeutic approach, primarily through the use of antibodies to A$\beta$. This approach involves either immunizing with A$\beta$ (Schenk D, et al. (1999) *Immunization with amyloid-$\beta$ attenuates Alzheimer-disease-like pathology in the PDAPP mouse*. Nature 400:173-177; Janus C, et al. (2000) *A peptide immunization reduces behavioral impairment and plaques in a model of Alzheimer's disease*. Nature 408:979-982; Morgan D et al. (2000) *A$\beta$ peptide vaccination prevents memory loss in an animal model of Alzheimer's disease*. Nature 408:982-985; Weiner H L, et al. (2000) *Nasal administration of amyloid-$\beta$ peptide decreases cerebral amyloid burden in a mouse model of Alzheimer's disease*. Ann Neurol 48:567-579; Das P, et al. (2001) *Reduced effectiveness of A$\beta$1-42 immunization in APP transgenic mice with significant amyloid deposition*. Neurobiol Aging 22:721-727) or through the passive administration of A$\beta$ antibodies (Bard F, et al. (2000) *Peripherally administered antibodies against amyloid $\beta$-peptide enter the central nervous system and reduce pathology in a mouse model of Alzheimer disease*. Nat Med 6:916-919; DeMattos R B, et al. (2001) *Peripheral anti-A$\beta$ antibody alters CNS and plasma A$\beta$ clearance and decreases brain A$\beta$ burden in a mouse model of Alzheimer's disease*. Proc Natl Acad Sci USA 98:8850-8855; DeMattos R B, et al. (2002) *Brain to plasma amyloid-$\beta$ efflux: a measure of brain amyloid burden in a mouse model of Alzheimer's disease*. Science 295:2264-2267). The promising results derived from A$\beta$ immunization studies in mice led to clinical trials using A$\beta$ immunization that initially appeared to produce beneficial results (Hock C, et al. (2003) *Antibodies against beta-amyloid slow cognitive decline in Alzheimer's disease*. Neuron. 38:547-54). However, several patients developed encephalitis (Greenberg S M, et al. (2003) *Alzheimer disease's double-edged vaccine*. Nat Med. 9:389-390) and the clinical trails were stopped. Consequently there exists a need to safely and effectively treat Alzheimer's disease.

One of the theories that immerged from the immunological studies was that passive immunization with A$\beta$ antibodies resulted in an efflux of A$\beta$ from the brain into the plasma producing a peripheral "sink effect", DeMattos et al., 2001, 2002. It has been shown that peripheral administration of an anti-A$\beta$ monoclonal antibody resulted in a rapid 1,000 fold increase in plasma A$\beta$ and a marked reduction in A$\beta$ deposition in the brain, DeMattos et al., 2001. Subsequently, it was shown that introduction of two A$\beta$-binding compounds, ganglioside GM1 and gelsolin, to bind plasma A$\beta$ in hAPP transgenic mice, resulted in a lowering of brain A$\beta$ levels by 50% or more (Matsuoka Y, et al. (2003) *Novel therapeutic approach for the treatment of Alzheimer's disease by peripheral administration of agents with an affinity to beta-amyloid.* J Neurosci. 23:29-33). In this study it was demonstrated that the lowering of brain Aβ by ganglioside GM1 was not due to ganglioside GM1 crossing the blood-brain barrier. It has also been shown that exogenous Aβ is rapidly transported from the CSF to plasma, exhibiting a half-time of ~30 min (Ghersi-Egea J F, et al. (1996) *Fate of cerebrospinal fluid-borne amyloid beta-peptide: rapid clearance into blood and appreciable accumulation by cerebral arteries.* J Neurochem. 67:880-883; Shibata M, et al. (2000) *Clearance of Alzheimer's amyloid-ss(1-40) peptide from brain by LDL receptor-related protein-1 at the blood-brain barrier.* J Clin Invest. 106:1489-99). Yet another example is to use a soluble receptor for advanced glycation end products (RAGE) in the blood to bind Aβ (Deane R. et al. (2003) *RAGE mediates amyloid-β peptide transport across the blood-brain barrier and accumulation in brain.* Nat. Med. 9, 907-913).

The present invention comprises methods of lowering plasma Aβ levels as a way to lower brain Aβ using peripheral expression of amyloid peptide inactivating enzymes, like neprilysin, on hematopoietic cells. The methods of lowering plasma Aβ comprise i) peripheral expression of an amyloid peptide inactivating enzyme in hematopoietic stem cells comprising a viral vector to infect bone marrow stem cells with a neprilysin-expressing or other Aβ-degrading peptidase-expressing construct; ii) coupling of neprilysin or other Aβ degrading peptidases to hematopoietic cells; iii) modifying amyloid peptide inactivating enzymes such that the enzyme will bind to hematopoietic cells; or iv) use of liposomes or other agents to introduce neprilysin or other Aβ degrading peptidases into hematopoietic cells.

SUMMARY OF THE INVENTION

The present invention addresses the need for a method of preventing and treating Alzheimer's disease by inactivating peripheral amyloid peptide.

In one aspect of the present invention, there is a method for the reducing amyloid peptide in the brain of a mammalian host comprising inactivating peripheral amyloid peptide by peripherally expressing an effective amount of an amyloid peptide inactivating enzyme to reduce, via efflux, amyloid peptide from the brain. Peptidase is a preferred amyloid peptide inactivating enzyme used in the aspects and embodiments of this invention. The peptidase may be introduced by ex vivo or in vivo techniques known by one of ordinary skill in the art.

In a preferred embodiment, the invention provides a method for reducing amyloid peptide in the brain comprising inactivating peripheral amyloid peptide by peripheral expression of amyloid peptide inactivating enzymes comprising the steps of:

a. generating a recombinant viral or plasmid vector comprising a nucleotide sequence encoding an amyloid peptide inactivating enzyme;

b. taking a sample of hematopoietic stem cells from a patient;

c. introducing ex vivo the recombinant viral or plasmid vector into one or more hematopoietic stem cells of the sample; and d. transplanting the hematopoietic stem cells of step c. into the patient, such that the amyloid peptide inactivating enzyme is expressed on the surface of hematopoietic cells or secreted from hematopoietic cells, In another preferred embodiment, there is a method of reducing amyloid peptide in the brain comprising inactivating peripheral amyloid peptide by peripheral expression of amyloid peptide inactivating enzyme comprising the steps of:

a. generating a recombinant viral or plasmid vector comprising a nucleotide sequence encoding an amyloid peptide inactivating enzyme operatively linked to a promoter; and b. introducing the vector into hematopoietic stem cells in vivo by injection, such that the amyloid peptide inactivating enzyme is expressed on the surface of or secreted from hematopoietic cells, In another aspect of the present invention, there are transduced stem cells for treating and/or preventing Alzheimer's disease. In a preferred embodiment stem cells are transduced with a vector encoding an amyloid peptide inactivating enzyme. Preferably the stem cells are hematopoietic stem cells. In a preferred embodiment the vector is a viral vector, and most preferably a lentivirus or adeno associated viral vector. In a preferred embodiment the amyloid peptide inactivating enzyme is a peptidase, and most preferably, the peptidase is neprilysin or a biologically active derivative or fragment thereof.

In another aspect of the invention, there is a method of reducing amyloid peptide in the brain comprising inactivating peripheral amyloid peptide by coupling amyloid peptide inactivating enzymes to hematopoietic cells. In a preferred embodiment, method comprises the steps of:

a. taking a sample of hematopoietic cells from a patient;

b. coupling one or more hematopoietic cells to one or more amyloid peptide inactivating enzyme ex vivo; and c. introducing the amyloid peptide inactivating enzyme-bound-hematopoietic cells into the blood of the patient;

Coupling may be performed by one of several methods. Preferably, the coupling is facilitated by biotinylation of the enzyme and the hematopoietic cells using streptavidin and/or avidin to couple biotin-bound molecules together. In another preferred method coupling is facilitated by chemical cross-linking reagents such as glutaraldehyde.

In another preferred embodiment the coupling is effected by modifying one or more enzyme so that it binds to one or more hematopoietic cell. Modification preferably includes coupling a C-terminal human red blood cell binding peptide sequence to amyloid peptide inactivating enzyme such that the C-terminal human RBC binding peptide sequence-bound enzyme couples with one or more hematopoietic cells. Modification also preferably includes coupling an antibody to hematopoietic cells to an amyloid peptide inactivating enzyme such that the antibody-bound enzyme couples with one or more hematopoietic cells. Modification also preferably includes coupling the C-terminal red blood cell binding peptide sequence to the enzyme, or coupling an antibody to hematopoietic cells to the enzyme. Modification also preferably includes adding an anchor, such as glycoinositol phospholipid (GPI), to an amyloid inactivating enzyme to permit insertion of the amyloid peptide inactivating enzyme into the membrane of a hematopoietic cell.

In another preferred aspect of the present invention, there is a method of reducing amyloid peptide in the brain comprising modifying in vitro one ore more amyloid peptide inactivating enzyme such that the modified amyloid peptide inactivating enzymes binds to one or more hematopoietic cells and introducing the one or more modified amyloid peptide inactivating enzyme coupled hematopoietic cells into the blood of a patient. Modification of the amyloid peptide inactivating enzyme comprise the methods disclosed herein and others that are known or become known to one skilled in the art of coupling molecules, preferably, coupling amyloid peptide inactivating enzymes to hematopoietic cells.

In still another aspect of the invention, there is a method of reducing amyloid peptide in the brain comprising inactivating peripheral amyloid peptide by introducing an amyloid peptide inactivating enzyme into hematopoietic cells of a patient via liposomes or other delivery reagents. The amyloid peptide inactivating enzyme-containing liposome may be delivered ex-vivo into the hematopoietic cells of a patient and then transplanted into a patient or delivered in vivo into the hematopoietic cells of a patient.

It is yet another aspect of the invention to provide methods for preventing and/or treating a patient with Alzheimer's disease utilizing the methods described herein to reduce levels or prevent accumulation of amyloid peptide in the brain. In one preferred embodiment, the method comprises administering (ex vivo or in vivo) to the hematopoietic stem cells of a patient in need thereof a therapeutically effective amount of a recombinant viral vector or plasmid vector comprising a nucleotide sequence encoding an amyloid peptide inactivating enzyme operatively linked to a promoter such that it is expressed on the surface of or secreted from hematopoietic cells. In another preferred embodiment, a therapeutically effective amount of stem cells transduced with a DNA vector encoding an amyloid peptide inactivation enzyme are administered to a patient. In another preferred embodiment, the method comprises administering to a patient in need thereof a therapeutically effective amount of an amyloid peptide inactivating enzyme to peripheral hematopoietic cells by the methods described herein to inactivate peripheral amyloid peptide resulting in a reduction, via efflux, of amyloid peptide from the brain.

These and other aspects of the invention will be more fully understood from the following description of the invention and the referenced drawings attached hereto.

BRIEF DESCRIPTION OF THE DRAWINGS

FIG. 5 B shows data in a repeat of the experiment. The NEP-lentivirus was used to transduce bone marrow stem cells from a donor mouse, which were transplanted into a two-month old recipient mouse to produce neprilysin expression on white blood cells. About 65% of the bone marrow cells used for transplantation expressed neprilysin. Cells in the M1 region are neprilysin positive cells. Control is a histogram of a recipient mouse without bone marrow transplantation. There are less than 2% cells appearing as neprilysin positive cells. The panel labeled NEP is a histogram of cells from a recipient mouse receiving NEP-lentivirus transduced bone marrow cells and shows greater than 20% of the white blood cells express neprilysin. The panel labeled NEPx is a histogram of cells from a recipient mouse receiving inactive NEP-lentivirus transduced bone marrow cells and shows greater than 20% of the white blood cells express inactive neprilysin FIG. 6 shows reduced Aβ in the brain from NEP peripherally expressed on white blood cells.

FIG. 10 shows that biotinylated NEP (as shown in FIG. 9) retains enzymatic activity.

FIG. 13 shows a modified form of neprilysin in which a C-terminal human red blood cell binding peptide sequence is attached. SS represents a secretion signal.

FIG. 15 shows a modified form of neprilysin in which a C-terminal single chain antibody directed against a red blood cell surface epitope sequence is attached.

DETAILED DESCRIPTION

Figure 1:
FIG. 1 illustrates a lentiviral virus construct used for expression of neprilysin on hematopoietic cells. Similar constructs can be used for expressing other Aβ degrading enzymes.

All patents, patent applications and literature cited in this description are incorporated in their entirety by reference herein. In the case of inconsistencies, the present disclosure, including definitions, will prevail.

As used herein, an "amyloid peptide" includes beta or gamma amyloid peptides (i.e., Aβ and Aγ, respectively). Preferably, the peptide is amyloid beta peptide. More preferably, the beta peptide is $A\beta_{1-40}$ or $A\beta_{1-42}$. Most preferably, the beta peptide is $A\beta_{1-42}$.

As used herein, an "amyloid peptide inactivating enzyme" encompasses a group of functionally or structurally related proteins that modulate, bind to, and/or hydrolyze amyloid peptides, and prevent the peptides from depositing as plaques or fibrils. Preferably, toxic side-effects are minimized. By "inactivating" it is meant that the enzyme may functionally prevent amyloid peptides from aggregating and from forming plaques. Preferably, "inactivating" refers to degrading, clearing and/or dissolution of the amyloid peptide, plaque or fibril. Preferably "degrading" or "clearing" refers to the act of changing a protein, like $A\beta$, or a protein complex, like amyloid plaques and fibrils, to a less complex protein or protein complex, respectively. Degradation of $A\beta$ is preferably by hydrolysis, a chemical process whereby a compound is cleaved into two or more simpler compounds with the uptake of the H and OH parts of a water molecule on either side of the chemical bond cleaved (e.g., insulysin as shown in U.S. Published Patent Application No. 2003/0165481). Degradation of $A\beta$ plaques may be caused by an equilibrium between fibrillary $A\beta$ and monomeric, dimeric or trimeric $A\beta$, the monomeric, dimeric and trimeric forms of $A\beta$ are hydrolyzed by neprilysin (Kanemitsu H, Tomiyama T, Mori H. (2003) *Human neprilysin is capable of degrading amyloid beta peptide not only in the monomeric form but also the pathological oligomeric form.* Neurosci Left. 350:113-116) thus "pulling" the $A\beta$ out of the plaque through equilibration with the monomer or low molecular oligomers and leading to a dissolution of the plaque. Preferably, the enzyme is a peptidase. Non-limiting examples of the enzyme include insulysin (also known as insulin degrading enzyme or IDE), neprilysin (also known to as endopeptidase 24.11, NEP, or CALLA), neprilysin 2 (also known as secreted endopeptidase, secNEP, or membrane metallo-endopeptidase-like 2), endopeptidase 24.15 (also known as thimet oligopeptidase 1), endopeptidase 24.16 (also known as neurolysin), endothelin converting enzyme, angiotensin converting enzyme (also known as dipeptidase A), plasmin, MMP-9 (also known as gelatinase B), or similar peptidases or a combination thereof.

As used herein, the terms "bind" or "link," or "binds" or "links", or "binding" or "linking" means any interaction between two or more molecules by covalent or noncovalent forces, Van der waals forces, electrostatic forces, and/or hydrostatic forces.

As used herein, the term "biologically active" in reference to a nucleic acid, protein, protein fragment or derivative thereof is defined as an ability of the nucleic acid or amino acid sequence to mimic a known biological function elicited by the wild type form of the nucleic acid or protein.

As used herein, the terms "coupling" or "coupled" or "couple" means any interaction, association with, attachment, conjugation, linking, or binding of one molecule (including compounds, labels and ligands, amino acid sequence, or nucleic acid sequence) to another molecule, by direct or indirect means, using reactive groups, either in the molecules per se or in a chemical or molecule added for that purpose, in such a way as to allow each of the molecules to function in their intended manners.

As used herein, the term "expression" means the detectable effect of a gene, like a nucleic acid sequence encoding a peptidase or biologically active derivative or fragment. The term "express" means to manifest the detectable effect of a gene. A gene may be expressed inside a cell, on the surface of a cell or be secreted by the cell.

As used herein, the terms "hematopoietic" and "hemopoietic" are used interchangeably and mean pertaining to or relating to the formation of blood cells.

As used herein, the terms "hematopoietic cells" and "hemopoietic cells" are used interchangeably herein and refer to any cell pertaining to or relating to the blood, including white blood cells (WBCs) that fight infection and inflammations (e.g., leukocytes, lymphocytes), red blood cells (RBCs) that carry oxygen (e.g., erythrocytes), and platelets that are responsible for blood clotting.

As used herein, "hematopoietic stem cell(s)", "hemopoietic stem cells", "hematopoietic progenitor cell(s)" and "hemopoietic progenitor cell(s)" are used interchangeably herein and refer to any precursor cell whose daughter cells may differentiate into various cells that are found in mammalian blood systems, including, white blood cells that fight infection and inflammations (e.g., leukocytes, lymphocytes), red blood cells that carry oxygen (e.g., erythrocytes), and platelets that are responsible for blood clotting.

As used herein, the term "inactivate" refers to the act of degrading, clearing and/or dissolving $A\beta$ from the periphery or the central nervous system.

As used herein, the term "maintenance", when used in the context of delivery to hematopoietic stem cells, denotes the ability of introduced DNA to remain present in the cell. When used in other contexts, it means the ability of targeted DNA to remain present in the targeted cell or tissue so as to impart a therapeutic effect.

As used herein, the term "mammalian host" includes members of the animal kingdom including but not limited to human beings.

As used herein, the term "operatively linked" refers to the linkage of a DNA segment to another DNA segment in such a way as to allow the segments to function in their intended manners. A DNA sequence encoding a gene product is operatively linked to a regulatory sequence when it is ligated to the regulatory sequence, such as, for example, promoters, enhancers and/or silencers, in a manner which allows modulation of transcription of the DNA sequence, directly or indirectly. For example, a DNA sequence is operatively linked to a promoter when it is ligated to the promoter downstream with respect to the transcription initiation site of the promoter, in the correct reading frame with respect to the transcription initiation site, and allows transcription elongation to proceed through the DNA sequence. An enhancer or silencer is operatively linked to a DNA sequence coding for a gene product when it is ligated to the DNA sequence in such a manner as to increase or decrease, respectively, the transcription of the DNA sequence. Enhancers and silencers may be located upstream, downstream or embedded within the coding regions of the DNA sequence. A DNA for a signal sequence is operatively linked to DNA coding for a polypeptide if the signal sequence is expressed as a preprotein that participates in the secretion of the polypeptide. Linkage of DNA sequences to regulatory sequences is typically accomplished by ligation at suitable restriction sites or via adapters or linkers inserted in the sequence using restriction endonucleases known to one of skill in the art.

As used herein, the term "patient" includes members of the animal kingdom including but not limited to human beings.

As used herein, the term "peripheral" or "periphery" means relating to the outside of, or being situated outside of, the central nervous system.

As used herein, a "promoter" can be any nucleotide sequence that is active, and controls transcription in a eukaryotic cell. The promoter may be active in either or both eukaryotic and prokaryotic cells. Preferably, the promoter is active in mammalian cells. Most preferably, the promoter is active in mammalian hematopoietic cells. The promoter may be constitutively expressed or inducible.

As used herein, a "selectable marker" includes a gene product that is expressed by a cell that stably maintains the introduced DNA, and causes the cell to express an altered phenotype such as morphological transformation, or an enzymatic activity. Isolation of cells that express a transfected gene is achieved by introduction into the same cells a second gene that encodes a selectable marker, such as one having an enzymatic activity that confers resistance to an antibiotic or other drug. Examples of selectable markers include, but are not limited to, thymidine kinase, dihydrofolate reductase, aminoglycoside phosphotransferase, which confers resistance to aminoglycoside antibiotics such as kanamycin, neomycin and geneticin, hygromycin B phosphotransferase, xanthine-guanine phosphoribosyl transferase, CAD (a single protein that possesses the first three enzymatic activities of de novo uridine biosynthesis—carbamyl phosphate synthetase, aspartate transcarbamylase and dihydroorotase), adenosine deaminase, and asparagine synthetase (Sambrook et al. *Molecular Cloning*, Third Edition Chapter 16. 2001), incorporated in its entirety by reference herein.

As used herein, the terms "stem cell(s)" and "progenitor cell(s)" are used interchangeably and mean any precursor cell whose daughter cells may differentiate into other cell types.

As used herein, the term "therapeutically effective amount" means an amount sufficient to inactivate amyloid peptide in the periphery and/or the central nervous system.

In one aspect the present invention discloses ex vivo and in vivo techniques for delivery and expression of a DNA sequence of interest to the periphery of a mammalian host. One of the ex vivo techniques involves culture of cells, in vitro transfection of the DNA sequence, DNA vector or other delivery vehicle of interest into the cells, followed by transplantation of the modified cells to the target joint of the mammalian host, so as to effect in vivo expression of the gene product of interest.

It will be understood by the artisan of ordinary skill that the preferred source of cells for treating a human patient is the patient's own tissues, such as autologous bone marrow, and preferably autologous hematopoietic stem cells. Hematopoietic stem cells may differentiate to white cells (e.g., leukocytes), red cells (e.g., erythrocytes) and platelets.

In one embodiment, the present invention provides a method of employing as the DNA sequence a gene capable of encoding an amyloid peptide inactivating enzyme or a biologically active derivative or fragment thereof, and employing as a vector any DNA vector known to one of ordinary skill in the art capable of stable maintenance within the targeted cell or tissue upon delivery, regardless of the method of delivery utilized. The method of this invention provides introducing at least one gene encoding an amyloid peptide inactivating enzyme into at least one cell of a target tissue for treating the mammalian host. Preferably the target tissue is bone marrow, and preferably the target cell is a hematopoietic stem cell, however, any progenitor cell may be targeted for delivery into liver, lung, kidney, muscle or other tissues in contact with blood. The method of this invention further provides transplantation of infected target cells into a mammalian host for expression of the amyloid peptide inactivating enzyme on cell surfaces. Preferably the amyloid peptide inactivating enzyme is expressed on the surface of, or secreted by, blood cells such as, platelets, red blood cells and white blood cells, or a combination of any of the foregoing. Most preferably, the amyloid peptide inactivating enzyme is expressed on red blood cells (e.g., erythroids, erythrocytes).

The amyloid peptide inactivating enzyme of the present invention is preferably a peptidase or a biologically active derivative or fragment thereof. The peptidase, including some biologically active variants thereof may be insulysin (also known as insulin degrading enzyme or IDE) [human IDE Genebank Accession # NM004969]; neprilysin (also known to as endopeptidase 24.11, NEP, or CALLA) [human NEP Genebank Accession #s NM000902, NM007287, NM007289, NM007288]; neprilysin 2 (also known as secreted endopeptidase, secNEP, or membrane metallo-endopeptidase-like 2) [human NEP2 Genebank Accession # NM033467]; endopeptidase 24.15 (also known as thimet oligopeptidase 1) [human endopeptidase 24.15 Genebank Accession # NM003249]; endopeptidase 24.16 (also known as neurolysin) [human endopeptidase 24.16 Genebank Accession # NM020726]; endothelin converting enzyme [human endothelin converting enzyme 1 Genebank Accession # NM001397; human endothelin converting enzyme 2 Genebank Accession # NM014693]; angiotensin converting enzyme (also known as dipeptidase A) [human angiotensin converting enzyme Genebank Accession #s NM 000789, NM152831, NM152830]; plasmin [human plasmin derived from human plasminogen Genebank Accession #000301]; MMP-9 (also known as gelatinase B) [human MMP-9 Genebank Accession # NM 004994], or similar peptidases. Preferably, the peptidase is neprilysin.

This invention also includes other biologically active derivatives or fragments (i.e., variants) of peptidases that are substantially identical polynucleotides that hybridize to the complement of a nucleic acid sequence encoding a peptidase under stringent hybridization conditions for the isolation of nucleic acids that encode peptidases that modulate and/or bind to an amyloid peptide, thereby inactivating the amyloid peptide. Highly stringent conditions involve hybridizing at 68° C. in 5×SSC/5×Denhart's solution/1.0% SDS, and washing in 0.2×SSC/0.1% SDS at room temperature. Moderately stringent conditions include washing in 3×SSC at 42° C. The parameters of salt concentration and temperature can be varied to achieve optimal level of identity between the primer and the target nucleic acid. Additional guidance regarding such conditions is readily available in the art, for example, Sambrook and Russel, Molecular Cloning, a laboratory manual, (3rd ed.), Cold Spring Harbor Laboratory Press, New York, (2001) and F. M. Ausubel et al eds., Current Protocols in Molecular Biology, John Wiley and Sons (1994).

The direct delivery of the DNA vector molecule to the target cell or tissue may be a viral or plasmid DNA vector molecule. This method includes employing the biologic means of utilizing a virus to deliver the DNA vector molecule to the target tissue. Preferably the virus is a pseudovirus, the genome having been altered such that the pseudovirus is capable only of delivery and stable maintenance within the target cell, but not retaining an ability to replicate within the target cell or tissue. Most preferably, the virus is attenuated, the strain having been selected for diminished virulence so as to not spread disease.

The viral genome may be further manipulated by recombinant DNA techniques such that the viral genome acts as a DNA vector molecule, which contains the heterologous gene of interest to be expressed within the target cell or tissue. In a preferred embodiment, the DNA vector molecule comprises the gene of interest, which may be operatively linked to a promoter, transcription enhancer and/or translation enhancer to either produce high-level expression or cell specific expression or both. Promoters, transcription and translation enhancers for high-level and/or cell specific expression are known to one of ordinary skill in the art. Preferably, the promoter is a white blood cell specific promoter. More preferably, the promoter is a red blood cell specific promoter. Most preferably, the promoter is ankyrin-1. Preferred enhancers include the GATA-1 and HS-40 used in tandem together with the ankyrin-1 promoter.

Non-limiting examples of preferred viral vectors include adenovirus vector, adeno-associated virus (AAV) vector, lentivirus, murine leukemia virus or herpes-simplex virus (HSV) vector, or other viral vectors currently in development, and preferably, replication deficient variants thereof. Preferably, the DNA viral vector is a lentivirus vector.

Non-limiting examples of preferred plasmid vectors include pcDNA, pCMV or any other mammalian cells expression plasmids containing the CMV promoter or other promoters.

Transplantation preferably occurs via injection of the transduced target cells into a mammalian host. The transduced target cells may be directly injected into the bone marrow tissue of the mammalian host. Direct intra-bone marrow injection of bone marrow stem cells has been described by Kushida T, Inaba M, Hisha H et al. *Intra-bone marrow injection of allogeneic bone marrow cells: a powerful new strategy for treatment of intractable autoimmune diseases in MRL/lpr mice*. Blood 2001; 97:3292-3299). Preferably transplantation is directed by intravenous injection of the transduced target cells into the blood of the mammalian host. The cells may enter bone and serves as a source of bone marrow stem cells. Such and other techniques for transplantation of the transduced target cells are known to one of ordinary skill in the art and are incorporated herein.

In a preferred embodiment, a lentivirus-neprilysin (lentivirus-NEP) construct is used to transduce hematopoietic stem cells derived from bone marrow, which transduced hematopoietic stem cells are then transplanted into a mammalian host. Transplantation occurs by intravenous injection of the infected stem cells into the circulatory system of the mammalian host. The transplanted neprilysin expressing stem cells continuously express neprilysin on hematopoietic cells, e.g., white and red blood cells. The expressed neprilysin degrades peripheral Aβ and results in a lowering of brain Aβ through a "sink effect". Without intending to be limited by theory, it is hypothesized that reduction of peripheral Aβ causes an imbalance in Aβ levels in the periphery and the CNS, resulting in Aβ from the brain to be drawn out of the CNS into the periphery as Aβ levels in the periphery decrease.

Transduction of Hematopoietic Stem Cells.

Transduction of hematopoietic stem cells is performed using bone marrow cells derived from a C57BL/6 donor mouse carrying the leukocyte common antigen variant CD45.1. These cells are transduced with a lentivirus-NEP. The transduced bone marrow cells are subsequently transplanted into a sublethally irradiated (600 rads for 3 min.) C57BL/6 recipient mouse that expresses the leukocyte common antigen variant CD45.2. Optimization of neprilysin expression is carried out by varying the multiplicity of infection (MOI) from 10 to 100 to 1000. Twenty four (24) mice may be used for these studies, 8 at each MOI. For each 8 at each MOI, the groups can be further subdivided into 4 males and 4 females to look for trends in expression based on sex differences, as sex differences in the extent of amyloid deposition have been reported in hAPP transgenic mice. (Callahan M J, et al. (2001) *Augmented senile plaque load in aged female beta-amyloid precursor protein-transgenic mice*. Am J Pathol. 158:1173-7; Lee J Y, et al. (2002)). Contribution by synaptic zinc to the gender-disparate plaque formation in human Swedish mutant hAPP transgenic mice. Proc Natl Acad Sci USA. 99:7705-10). If a trend is observed the study may be expanded to include eight to ten males and eight to ten females at each MOI. Transfer of the CD45.1 antigen from the donor mouse to recipient mice that contain the CD45.2 variant of this antigen was measured. Both the CD45.1 and CD45.2 variants are detected in blood by flow cytometry using fluorescein isothiocyanate (FITC) conjugated antibodies and Phycoerythrin (PE) conjugated antibody from Pharmingen.

Expression of Neprilysin on Hematopoietic Cells.

Blood is collected by retro orbital bleeding into heparinized tubes, and diluted with PBS and dextran, the latter to 0.7% final concentration. The red blood cells and/or white blood cells are collected after incubation at 37° C. and resuspended in PBS for flow cytometry analysis for neprilysin using an FITC conjugated monoclonal antibody CLB-CALLA/1,4F9 from Research Diagnostics Inc. and for neprilysin activity measurements as noted below. The supernatant is used to measure the percent of CD45.1 positive cells by flow cytometry. We have previously shown that dilution of purified neprilysin into heparinized tubes does not affect its enzymatic activity (data not included) thus validating the ability to collect blood from animals and measure neprilysin activity without complications and artifacts from the collection method. It may be advantageous to lyse the red blood cells and isolate plasma membranes by centrifugation at 100,000×g for 1 hr. The membrane fraction contains the neprilysin activity, which was confirmed in initial preliminary experiments.

Measuring Neprilysin Activity.

Neprilysin activity is measured with glutaryl-Ala-Ala-Phe-X where X=AMC (aminomethylcoumarin), MNA (methoxynaphthylamine) or -pNA (para-nitroaniline) as a specific synthetic substrate (Li C, Hersh L B. (1995) *Neprilysin: assay methods, purification, and characterization*. Methods Enzymol. 248:253-63.). Neprilysin cleaves glutaryl-Ala-Ala-Phe-X releasing glutaryl-Ala-Ala and Phe-X. The reaction is stopped and the Phe-X is secondarily cleaved to free Phe and either the highly fluorescent AMC=aminomethylcoumarin or methoxynaphthylamine groups or the visible para-nitroaniline by an added aminopeptidase, aminopeptidase M. The released aminomethylcoumarin or methoxynaphthylamine is quantitated fluorometrically while the released para-nitroaniline is quantitated spectrophotometrically.

A modified one-step continuous assay using a recombinant aminopeptidase produced in the Hersh laboratory may be used in place of the two-step assay (Li and Hersh, 1995). The recombinant aminopeptidase is added directly to the assay in excess such that the reaction is monitored continuously. Thompson, M. W. and Hersh L. B., *Analysis of conserved residues of the human puromycin-sensitive aminopeptidase*. Peptides. 2003 September; 24(9):1359-65; Ma Z, et al. *Proteolytic cleavage of the puromycin-sensitive aminopeptidase generates a substrate binding domain*. Arch Biochem Biophys. 2003 Jul. 1; 415(1):80-6; Thompson M W, Govindaswami M, Hersh L B. *Mutation of active site residues of the puromycin-sensitive aminopeptidase: conversion of the enzyme into a catalytically inactive binding protein*. Arch Biochem Biophys. 2003 May 15; 413(2):236-42. The one-step assay has been further modified for use in a 96 or 384 well fluorescence plate reader. This modified assay is about 10 times more sensitive than the discontinuous assay, it permits linear initial rates to be measured, and it accommodates multiple samples to be assayed at the same time. The neprilysin inhibitors thiorphan and phosphoramidon are used to determine the specificity of the reaction.

Once an optimal multiplicity of infection (MOI) is established, the time course for expression of neprilysin from one to twelve months is determined by both fluorescence activated cell sorting (FACS) and determination of enzyme activity. Neprilysin levels at 1, 2, 4, 6, 9, and 12 months from blood obtained through orbital bleeding is measured. This follows since it has been shown that the peripheral administration of Aβ binding agents (gelsolin or ganglioside GM1) lowered Aβ levels within a month (Matsuoka et al., 2003).

Non-Tg C57BL/6 mice for optimizing expression of neprilysin on bone marrow stem cells may be used and to minimize the cost involved in producing or purchasing hAPP Tg mice. C57BL/6NCr mice are obtained from the National Cancer institute-Frederick, Animal Production Program, Frederick, Md.

Transplantation and Analyzing Aβ Levels.

Once the expression of neprilysin has been optimized in C57BL/6 mice the optimal parameters are used to express neprilysin in the J20 or other hAPP transgenic mouse lines, i.e. the 3x-Tg mouse of Oddo et al. (*Triple-transgenic model of Alzheimer's disease with plaques and tangles: intracellular Abeta and synaptic dysfunction*. Neuron. 39:409-421 (2003)). Bone marrow transplantation is performed into mice two months of age and measure Aβ levels every month out to eighteen months. Plasma is obtained either through orbital bleeding or tail bleeding into heparinized tubes without sacrificing the animals, or if necessary from trunk blood after sacrifice. The method of obtaining blood and therefore the number of animals required depends on the Aβ levels and the sensitivity of our assay. Plasma is obtained by centrifugation at 1,000×g for 10 min and used for Aβ determination. The plasma Aβ levels in J20 or other hAPP Tg mice receiving bone marrow cells transduced with wild type neprilysin is compared to J20 or other hAPP mice receiving lentivirus expressing an E585V neprilysin mutant, which is an inactive form of the enzyme.

The plasma Aβ levels are determined by sandwich ELISA. Commercial ELISA kits from Biosource International or ELISA plates produced in the laboratory from commercially available antisera can be used. These are mouse monoclonal antibodies 6E10 and 4G8 to human amyloid beta protein, or a rabbit polyclonal antibody to specific to Aβ 40 or specific to Aβ 42 respectively, obtained from Signet, (Dedham, Mass.) to measure total Aβ, as well as measuring $A\beta_{40}$ and $A\beta_{42}$. To determine the fraction of Aβ present as oligomers, the plasma sample is subjected to PAGE using Tricine gels commercially available from Invitrogen and immunostained with monoclonal antibody 6E10 (Signet Pathology Systems, Inc.) or our own polyclonal antisera made to Aβ residues 21 to 30.

Analyzing Expression of Neprilysin on Hematopoietic Cells on Brain Aβ Levels and Amyloid Deposition in the Brain of hAPP Transgenic Mice Having determined the time course and to what extent plasma Aβ levels can be decreased by expression of neprilysin on hematopoietic cells, the effect of this peripheral neprilysin expression on brain Aβ levels is tested. Forty eight (48) two-month old hAPP transgenic mice (i.e., the J20 mouse or the "triple transgenic" mouse of Oddo S et al. *triple-transgenic model of Alzheimer's disease with plaques and tangles: intracellular Abeta and synaptic dysfunction*. Neuron. 39:409-421 (2003)), half undergoing bone marrow transplantation with stem cells expressing neprilysin and the other half undergoing bone marrow transplantation with stem cells expressing the inactive E585V mutant neprilysin are used. Six mice in each group (active versus inactive neprilysin) are sacrificed at 3 month intervals for up to eighteen months following maximal neprilysin expression. The brains from these mice are collected and used to measure total brain Aβ, $A\beta_{1-40}$ and $A\beta_{1-42}$ levels. For measuring Aβ levels, the Aβ peptides are extracted with formic acid according to the procedure of Refolo L M, et al. *Hypercholesterolemia accelerates the Alzheimer's amyloid pathology in a transgenic mouse model*. Neurobiol. Dis. 7:321-31 (2000), or with guanidine (Masliah E, et al. *beta-amyloid peptides enhance alpha-synuclein accumulation and neuronal deficits in a transgenic mouse model linking Alzheimer's disease and Parkinson's disease*. Proc Natl Acad Sci USA. 2001 Oct. 9; 98(21):12245-50) and then determined by sandwich ELISA using kits available from Biosource International. To determine the fraction of Aβ present as oligomers, the sample is subjected to PAGE using Tricine gels (commercially available from Invitrogen) and immunostained with monoclonal antibody 6E10 (Signet Pathology Systems, Inc.) or our own polyclonal antisera made to Aβ residues 21 to 30.

Another group of thirty experimental and thirty control mice are treated in a similar manner as above except that Aβ deposition in these animals is measured. In both the J20 hAPP and the 3x-Tg mouse Aβ amyloid deposition is observed at about 6 to 9 months of age and increases thereafter. Therefore bone marrow transplantation is performed at about 2-3 months of age and the mice are euthanized at 6, 9, 12, 15 and 18 months of age in groups of 6. The mice are perfused transcardially with 4% paraformaldehyde, the brains removed and fixed overnight at 4° C. The fixed brains are rinsed in PBS, dehydrated, and then embedded in paraffin and sectioned. Histological staining with hematoxylin-eosin, cresyl-violet or silver impregnation as described by Bruce et al. (1996) is performed. Bruce, A. J. et al. (1996) *Altered neuronal and microglial responses to excitotoxic and ischemic brain injury in mice lacking TNF receptors*. Nat. Med. 2: 788-794. Amyloid deposits are detected in cryostat sections by incubation overnight at 4° C. with biotinylated mouse monoclonal antibodies 4G8) from (Signet, Dedham, Mass.), The Elite kit from Vector Laboratories is used to detect binding of the primary antibody. Sections are counterstained with hematoxylin/eosin and examined with a Nikon light microscope. A minimum of ten sections per mouse are examined. The number of plaques are counted and the size of the plaques in the hippocampus are measured.

Analyzing Effect of Expression of Neprilysin on Hematopoietic Cells and the Number of Amyloid Plaques in Older hAPP Tg Mice.

To demonstrate the hypothesis that lowering of brain Aβ levels through peripheral expression of neprilysin in the plasma of older hAPP Tg mice leads to a decrease in the number of preformed amyloid deposits, the same basic protocol as set forth above is used except that the recipient hAPP transgenic mice (i.e. J20 mice) are 18-20 months old, a time in which amyloid deposits are numerous in this transgenic line. Bone marrow stem cells are transduced at the optimal viral MOI and then bone marrow transplantation is performed into the older J20 mice as described herein. Plasma Aβ levels through analysis of blood obtained through orbital or tail vein bleeding. Once the plasma Aβ levels have been decreased to a steady-state level, the animals are sacrificed at various times (1 to 3 months initially) to determine if clearance of plasma Aβ has reversed amyloid plaque deposition in the brain. In our studies with direct expression of neprilysin in the brains of older mice (Marr et al, 2002), a decrease in the number of amyloid plaques was observed within a month. Ten (10) mice expressing wild type neprilysin on red blood cells are compared to ten (10) mice expressing the inactive mutant neprilysin on red blood cells at one month, three months, six months, and then at 6 month intervals until 2 years of age if feasible.

Transcardial perfusion with 4% paraformaldehyde is used after which the brains are removed and fixed. The fixed brains are rinsed in PBS, dehydrated, and then embedded in paraffin. Histological staining is performed on the paraffin embedded sections, with amyloid deposits detected with biotinylated mouse monoclonal antibodies 3D6 and 10D5 as noted above. Counterstained sections are quantitated with a Nikon light microscope. At least ten sections per mouse are used where the number, size, and appearance of plaques in the hippocampus determined. To ensure that the results obtained are not unique to the particular HAPP mouse line, (i.e. the J20 mouse) hAPP$^{SWE}$-presenilin-1 mice commercially available from Jackson labs or the triple transgenic mouse line will be used as controls.

In Vivo Delivery of Amyloid Peptide Inactivating Enzyme.

In another embodiment the present invention involves direct in vivo delivery of an amyloid peptide inhibiting enzyme gene to the bone marrow tissue of a mammalian host through use of either an adenovirus vector, adeno-associated virus (AAV) vector, lentivirus, or herpes-simplex virus (HSV) vector, murine leukemia virus (MuLV) or other viral vectors currently in development. In this embodiment, a DNA sequence of interest encoding a functional amyloid peptide inhibiting enzyme or enzyme fragment is subcloned into the respective viral vector. The amyloid peptide inhibiting enzyme gene containing viral vector is then grown to adequate titer and introduced into the bone marrow, preferably by injection into blood. In an exemplary procedure, the region from the inguen to the knee joint is shaved, and a 5-mm incision is made on the thigh. The knee is flexed to about a 90° angle, and the proximal side of the tibia is drawn to the anterior. A 26-gauge needle is inserted into the joint surface of the tibia through the patellar tendon and then inserted into the BM cavity. Using a microsyringe (50 µl; Hamilton Co.; Reno, Nev.). Bone marrow cells are injected from the bone holes into the bone marrow cavities of both tibiae.

Direct bone marrow tissue injection of a DNA molecule containing the gene of interest results in transfection of the recipient bone marrow tissue cells and hence bypasses the requirement of removal, in vitro culturing, transfection, selection, as well as transplanting the DNA vector containing hematopoietic stem cells to promote stable expression of the heterologous gene of interest.

In another embodiment, and as an additional alternative to the in vitro manipulation of hematopoietic stem cells, the gene encoding the product of interest is introduced into the area of bone marrow tissue as naked DNA. The naked DNA enters the bone marrow tissue cells, preferably hematopoietic stem cells, resulting in an in vivo gene expression of the amyloid peptide inhibiting enzyme on hematopoietic cells.

Coupling Amyloid Peptide Inactivating Enzyme to Hematopoietic Cells.

In another aspect the present invention provides methods of reducing amyloid peptide in the brain comprising inactivating peripheral amyloid peptide by coupling amyloid peptide inactivating enzymes to hematopoietic cells. Without intending to be bound by theory, by coupling one or more amyloid peptide inactivating enzyme to one or more hematopoietic cell the amyloid peptide inactivating enzyme is not degraded in vivo so rapidly. The longer the amyloid peptide inactivating enzyme is in circulation increases the opportunity of the amyloid peptide inactivating enzyme coming into contact with peripheral Aβ and inactivating the peripheral Aβ.

The present invention discloses ex vivo and in vivo techniques for coupling amyloid peptide inactivating enzyme with hematopoietic cells. Generally, the ex vivo techniques involve taking a sample of hematopoietic cells, in vitro coupling of one or more amyloid peptide inactivating enzyme to one or more hematopoietic cell, followed by transplantation of the sample having amyloid peptide inactivating enzyme-bound hematopoietic cells to the mammalian host, so as to effect increased presence and activity of peripheral amyloid peptide inactivating enzyme. It will be understood by the artisan of ordinary skill that the preferred source of hematopoietic cells for treating a human patient is the patient's own hematopoietic cells, such as red and white blood cells.

There are many techniques known by the skilled artisan for coupling one or more molecule or compound to another, which may be used to practice the present invention. In one preferred embodiment, coupling may be achieved by biotinylating one or more amyloid peptide inactivating enzyme and one or more hematopoietic cell of a mammalian host, and linking the biotin of one or more of each the enzyme and the hematopoietic cell using streptavidin and/or avidin, in accordance with the protocol set forth and incorporated in its entirety by reference herein (Dominici S, et al. *Red blood cell-mediated delivery of recombinant HIV-1 Tat protein in mice induces anti-Tat neutralizing antibodies and CTL*. Vaccine. May 16; 21(17-18):2073-81 (2003)). Other cross-linking reagents may also be used to link the two molecules to effect coupling of enzyme and hematopoietic cells. Non-limiting examples of such other cross-linking reagents include glutaraldehyde, (Perez M T et al. *In vivo studies on mouse erythrocytes linked to transferrin*. IUBMB Life. 2002 September; 54(3):115-21).

In another preferred embodiment, coupling may be achieved by modifying one or more amyloid peptide inactivating enzyme such that the modified enzyme binds to one or more hematopoietic cell. Preferably, one or more amyloid peptide inactivating enzyme is modified to contain a C-terminal human red blood cell binding peptide sequence as described in, and incorporated in its entirety by reference herein, Garcia J E, et al. *Peptides from the Plasmodium falciparum STEVOR putative protein bind with high affinity to normal human red blood cells*. Peptides. 2005 July; 26(7): 1133-43; Lopez R, et al. *Plasmodium falciparum: red blood cell binding studies of peptides derived from histidine-rich KAHRP-I, HRP-II and HRP-III proteins*. Acta Trop. 2000 May 31; 75(3):349-59. It is also preferable to modify one or more amyloid peptide inactivating enzyme such that it is coupled or bound to an antibody to a hematopoietic cell in accordance with the methods described in, and incorporated in its entirety by reference herein, Spitzer D, et al., *ScFv-mediated in vivo targeting of DAF to erythrocytes inhibits lysis by complement*. Mol Immunol. 2004 February; 40(13): 911-9. An antibody to a hematopoietic cell may be an antibody to a red blood cell or a white blood cell, or a platelet or capable of binding all three. Due to such modifications, the modified enzymes are able to couple to one or more hematopoietic cell.

In another preferred embodiment, coupling may be achieved by modifying one or more amyloid peptide inactivating enzyme such that the modified enzyme contains a glycoinositol phospholipid (GPI) that permits direct insertion of the protein into the membrane of one or more hematopoietic cells. Preferably, one or more amyloid peptide inactivating enzyme is modified to contain a GPI anchor as described in and incorporated herein by reference Howell S, Lanctot C, Boileau G, and Crine P, *Expression of an enzymatically active*

*glycosylphosphatidylinositol-anchored form of neutral endopeptidase* (EC 3.4.24.11) *in Cos-1 cells*, Biochem. J. (1994) 299:171-176.

In vivo techniques for coupling one or more amyloid peptide inactivating enzyme to one or more hematopoietic cell of a mammal involve, modifying in vitro one or more amyloid peptide inactivating enzyme such that it will bind to one or more hematopoietic cell and introducing the modified amyloid peptide inactivating enzyme into a mammalian host, preferably by injection into the blood or bone marrow. Amyloid peptide inactivating enzymes are modified as described above or in any such other manner so that the modified enzyme is capable of coupling with or to one or more hematopoietic cell.

Pharmacological Agents to Induce Synthesis or Activity of Amyloid Peptide Inactivating Enzyme.

In another aspect the present invention provides the use of pharmacological agents to induce synthesis of the endogenous gene encoding peripheral amyloid peptide inhibiting enzyme. Such a pharmacological substance may be a compound that "up regulates" or enhances the expression of peripheral amyloid peptide inhibiting enzyme. The pharmacological agent may bind to the regulatory region of the gene encoding the peripheral enzyme and thus activate its gene expression. Thus, the compound may be a transcriptional activator of the gene encoding the enzyme. Or, the compound may have a regulatory effect post transcriptionally in, for example, stabilizing the amyloid peptide inhibiting enzyme structure.

In still another aspect, pharmacological agents can be used to increase the activity of the peripheral amyloid peptide inhibiting enzyme. Such a pharmacological substance may be a compound that enhances the activity of the peripheral amyloid peptide inhibiting enzyme. The pharmacological agent may modulate the activity of the amyloid peptide inactivating enzyme, causing an increase in activity of the peripheral amyloid peptide inhibiting enzyme. Amyloid peptide inactivating enzyme enhancing substances may be bound to either one or both of amyloid peptide inactivating enzymes modified to couple with hematopoietic cells and hematopoietic cells for enhanced peripheral amyloid peptide inactivating activity.

The pharmacological agent may be placed in pharmaceutically acceptable excipient or carrier and administered to a person or individual in need thereof. Depending on the specific clinical status of the disease, administration can be made via any accepted systemic delivery system, for example, via oral route or parenteral route such as intravenous, intramuscular, subcutaneous or percutaneous route, or vaginal, ocular or nasal route, in solid, semi-solid or liquid dosage forms, such as for example, tablets, suppositories, pills, capsules, powders, solutions, suspensions, cream, gel, implant, patch, pessary, aerosols, collyrium, emulsions or the like, preferably in unit dosage forms suitable for easy administration of fixed dosages. The pharmaceutical compositions include a conventional carrier or vehicle and the pharmacological compound and, in addition, may include other medicinal agents, pharmaceutical agents, carriers, adjuvants, and so on.

If desired, the pharmaceutical composition to be administered may also contain minor amounts of non-toxic auxiliary substances such as wetting or emulsifying agents, pH buffering agents and the like, such as, by non-limiting example, sodium acetate, sorbitan monolaurate, triethanolamine oleate, and so on.

The compounds of this invention are generally administered as a pharmaceutical composition comprising a pharmaceutical vehicle in combination with the pharmacological compound. The amount of the drug in a formulation can vary within the full range employed by those skilled in the art, e.g., from about 0.01 weight percent (wt %) to about 99.99 wt % of the drug based on the total formulation and about 0.01 wt % to 99.99 wt % excipient.

The preferred mode of administration, for the conditions mentioned above, is oral administration using a convenient daily dosage regimen, which can be adjusted according to the degree of the complaint. For said oral administration, a pharmaceutically acceptable, non-toxic composition is formed by the incorporation of the selected pharmacological compound in any of the currently used excipients, such as, for example, pharmaceutical grades of mannitol, lactose, starch, magnesium stearate, sodium saccharine, talc, cellulose, glucose, gelatin, sucrose, magnesium carbonate, and the like. Such compositions take the form of solutions, suspensions, tablets, pills, capsules, powders, sustained release formulations and the like. Such compositions may contain between 0.01 wt % and 99.99 wt % of the active compound according to this invention.

Preferably the compositions have the form of a sugar coated pill or tablet and thus contain, along with the active ingredient, a diluent such as lactose, sucrose, dicalcium phosphate, and the like; a disintegrant such as starch or derivatives thereof; a lubricant such as magnesium stearate and the like; and a binder such as starch, polyvinylpyriolidone, acacia gum, gelatin, cellulose and derivatives thereof, and the like.

It is understood that by "pharmaceutical composition", it is meant that the pharmacological compound is formulated into a substance that is to be administered purposefully for modulating amyloid peptide inactivating enzymes to inactivate peripheral amyloid protein. The mode of action is believed to be by hydrolytic cleavage of the amyloid peptide by the amyloid inactivating enzyme U.S. Published Patent Application No. 2003/0165481 published on Sep. 3, 2004. However, it is understood that the pharmacological compound per se will not have a toxic effect, and by "pharmaceutical composition", it excludes those compositions that are used to administer to individuals as test compounds for a purpose other than as an inducer of inactivation of the amyloid protein.

Treating and/or Preventing Alzheimer's Disease

It is another aspect of the present invention to treat and/or prevent Alzheimer's Disease. In one embodiment, the method comprises administering to a patient in need thereof a therapeutically effective amount of stem cells transduced with a DNA vector encoding an amyloid peptide inactivation enzyme as described herein. Preferably the stem cells are hematopoietic stem cells including but not limited to red blood cells, white blood cells, and platelets. Preferably the DNA vector is a viral vector, and most preferably a lentivirus vector or an adeno associated virus vector. It is also preferable that the amyloid peptide inactivating enzyme is a peptidase, and most preferably, the peptidase is neprilysin or a biologically active derivative or fragment thereof. In another preferred embodiment, the method comprises administering (ex vivo or in vivo) to the hematopoietic stem cells of a patient in need thereof a therapeutically effective amount of a recombinant viral vector or plasmid vector comprising a nucleotide sequence encoding an amyloid peptide inactivating enzyme operatively linked to a promoter such that it is expressed on the surface of or secreted from hematopoietic cells.

In another embodiment, the present invention provides a method for treating and/or preventing Alzheimer's disease by administering to the hematopoietic cells of a patient in need thereof a thereapeutically effective amount of amyloid peptide inactivating enzyme. Preferably the enzyme is administered by coupling amyloid peptide inactivating enzyme to hematopoietic cells as described herein. Coupling may be performed ex vivo and then the enzyme-coupled hematopoietic cells are transplanted in to a patient, or it may occur in vivo via modified amyloid peptide inactivating enzymes. Preferably, coupling is performed ex vivo via biotinylation of amyloid peptide inactivating enzyme and hematopoietic cells and using streptavidin and/or avidin to link one or more biotinylated enzyme to one or more hematopoieteic cell. Coupling is preferably performed in vivo by modifying amyloid peptide inactivating enzyme and introducing the modified enzyme into a patient. Preferably, amyloid peptide inactivating enzyme is modified to contain either a C-terminal human red blood cell binding peptide sequence, or a glycoinositol phospholipids (GPI) anchor. It is also preferable to bind an antibody to a hematopoietic cell to an amyloid peptide inactivating enzyme to produce a chimeric protein in which the antibody combining region is directed against a hematopoietic cell surface protein. Preferably the modified enzyme is introduced by injection into the blood of a patient.

In another embodiment, there is a method for treating and/or preventing Alzheimer's disease by administering to the blood of a patient a therapeutically effective amount of an amyloid peptide inactivating enzyme-containing liposome or other delivery agent. Preferably, the amyloid peptide inactivating enzyme-containing liposomes introduce the enzyme into hematopoietic cells of the patient. The amyloid peptide inactivating enzyme-containing liposome may be delivered ex-vivo into the hematopoietic cells of a patient and then transplanted into a patient or delivered in vivo into the hematopoietic cells of a patient.

EXAMPLE 1

Lentivirus Constructs for Expression in Hematopoietic Cells

Lentivirus constructs for expression in hematopoietic cells were generated as described by Dull T, et al. *A third-generation lentivirus vector with a conditional packaging system.* J Virol. 1998 November; 72(11):8463-71.). Vector plasmids were constructed for the production of third generation lentiviral vectors. All vectors were designed to be self-inactivating and used the woodchuck hepatitis virus post-transcriptional regulatory element (WPRE) 3' to the transgene. The human cytomegalovirus (CMV) promoter was used to drive expression of the transgenes. The HIV-1 central poly-purine track were also located 5' to the promoter. Lentiviral vectors were produced using a four plasmid transfection system, as described by Dull et al. 1998. Briefly, 293T cells were transfected with vector and packaging plasmids, the supernatants are collected, and vectors are concentrated by centrifugation. The lentiviral vector titers were estimated by measuring the amount of HIV p24 gag antigen with an ELISA kit (Zeptometrix Co., Buffalo, N.Y.). FIG. 1 illustrates an exemplary lentiviral vector construct used for expression of NEP on hematopoietic cells.

EXAMPLE 2

Lentivirus Constructs for Expression in Red Blood Cells

Figure 8:
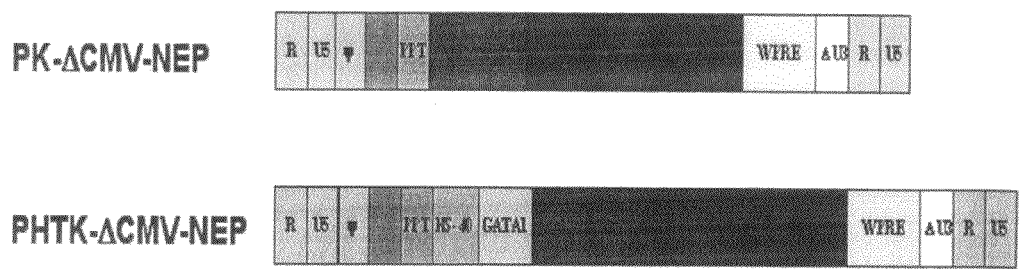
FIG. 8 (A-B) illustrates lentiviral virus constructs for expression of neprilysin on red blood cells. Similar constructs can be used for expressing other Aβ degrading enzymes.
Figure 9:
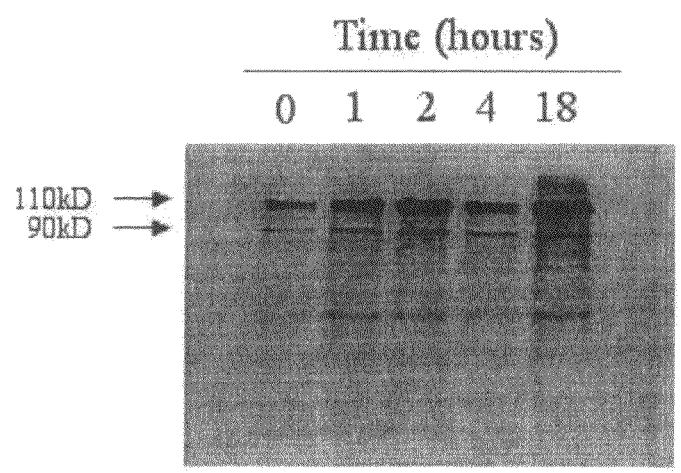
FIG. 9 shows the time course of NEP biotinylation with biotin-N-hydroxysuccinimide

Lentivirus constructs for expression in red blood cells were generated in the laboratory of Dr. Punam Malik of UCLA according to the methods described in and incorporated in their entirety by reference herein to Hanawa H, et al. (2002) *High-level erythroid lineage-directed gene expression using globin gene regulatory elements after lentiviral vector-mediated gene transfer into primitive human and murine hematopoietic cells.* Hum Gene Ther. 13:2007-2016, and Moreau-Gaudry F, et al. (2001) *High-level erythroid-specific gene expression in primary human and murine hematopoietic cells with self-inactivating lentiviral vectors.* Blood 98:2664-2672. These are self-inactivating lentiviral vectors that use an erythroid specific enhancer in combination with the woodchuck hepatitis virus post regulatory element and produce erythroid specific expression in both murine and human cell lines. In a preferred embodiment, the lentivirus constructs contain ankyrin-1 promoter in combination with two enhancers in tandem (the GATA-1 and HS-40). FIG. 8 (A-B) illustrates exemplary lentiviral constructs for the expression of NEP on red blood cells.

EXAMPLE 3

Neprilysin in Genetic Therapy Approach to Treat Alzheimer's Disease (AD)

Figure 2:
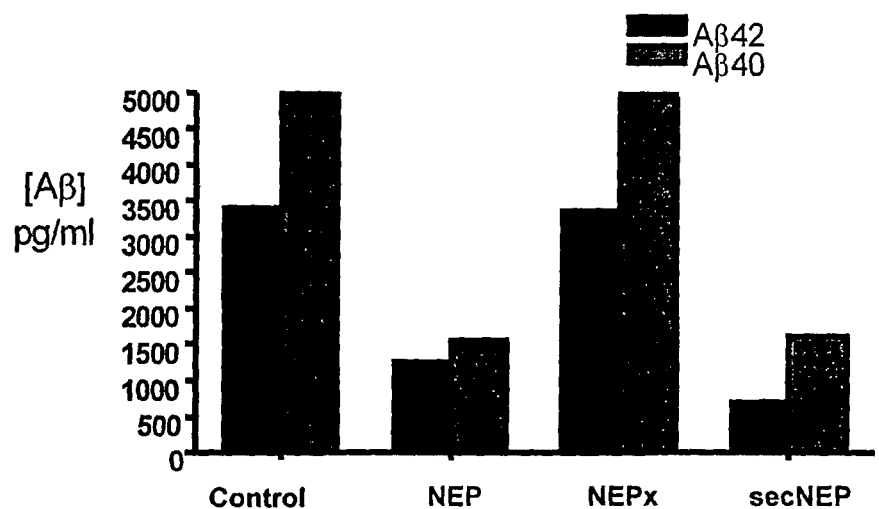
FIG. 2 illustrates that the expression of neprilysin (NEP) in Aβ secreting CHO cells (7PA2) efficiently reduces Aβ in the media. NEPx is an inactive point mutant of neprilysin on the cell surface. SecNEP is an engineered secreted form of neprilysin. NEP is wild type neprilysin on the cell surface.
Figure 3:
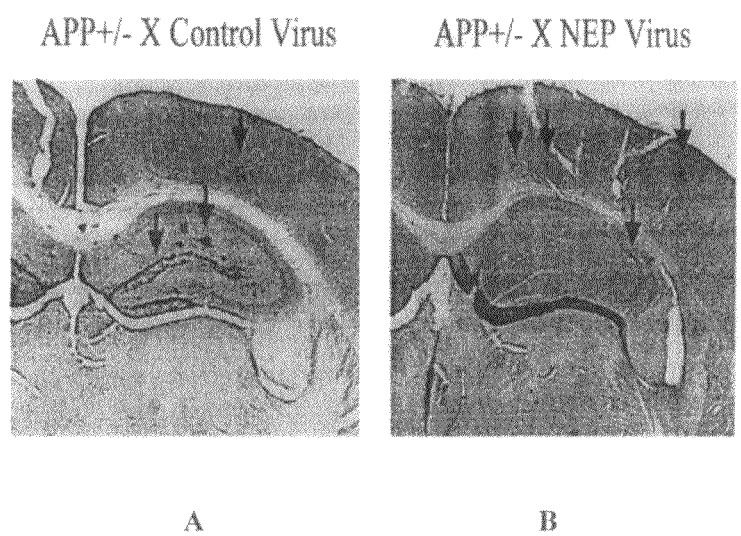
FIG. 3 illustrates Aβ deposits in the 9-month control (lentivirus-GFP) (FIG. 3A, left) or lentivirus-NEP transduced (FIG. 3B, right) J20 hAPP transgenic mouse. The arrows indicate Aβ deposits, which are numerous and dense in the control virus treated mouse. In the lentivirus-NEP treated brain there is a small amount of diffuse light staining material.

To evaluate the use of neprilysin as a potential candidate for a gene therapeutic approach for treating AD, the following lentivirus constructs were tested, comprising: (1) the neprilysin gene (NEP), (2) an inactive point mutant of neprilysin (NEPx), (3) a secreted form of neprilysin (SecNEP) that produces the extracellular domain, and (4) green fluorescent protein (GFP), each driven by the cytomegalovirus (CMV) promoter. These constructs were initially tested in a Chinese hamster ovary (CHO) cell line, 7PA2, (obtained from Dr. Dennis Selkoe) that is stably transfected with hAPP and that secretes relatively large amounts of Aβ into the media. As shown in FIG. 2, transduction of CHO 7PA2 cells with lentivirus expressing neprilysin or the secreted form of neprilysin produces a large decrease in the concentration of $A\beta_{1-42}$ and $A\beta_{1-40}$ in the media. In contrast, the inactive form of neprilysin produced no significant effect. We further found that transduction of the CHO 7PA2 cell line at a low multiplicity of infection, about 1 multiplicity of infection (MOI), produced a similar effect to that shown in FIG. 2 indicating that even low level expression of neprilysin is sufficient to efficiently degrade extracellular Aβ. Dr. Selkoe's group has recently measured the kinetics of Aβ hydrolysis by neprilysin using an Aβ analog (Leissring M A, et al. (2003) *Kinetics of amyloid beta-protein degradation determined by novel fluorescence- and fluorescence polarization-based assays.* J. Biol Chem. 278:37314-20) and found a Km of about 10 µM.

EXAMPLE 4

Transduction of Murine Bone Marrow Cells and Bone Marrow Transplantation

Bone marrow was harvested from 6-week-old C57BI/LY5.1 mice (B/6.SJL-CD45a-Pep3b, Jackson Laboratory, Bar Harbor, Me.) (CD45.11) by flushing femurs and tibiae. Lineage-negative cells were purified with the Hematopoietic Progenitor Enrichment kit from Stemcell Technologies. Enriched progenitor cells were prestimulated with Iscove's modified Dulbecco's medium (IMDM; Gibco, Grand Island, N.Y.) supplemented with 10% FCS containing 10 ng/mL of each of the following cytokines: mIL3, mIL6, hFlt3 ligand and 50 ng/ml hSCF (R&D, Minneapolis, Minn.) overnight and then transduced with lentiviral vectors two times at 24-hour intervals. On day 3, cells were washed twice with phosphate buffered saline (PBS) and $2\times10^5$ hematopoietic cells/mouse were injected into the tail vein of 8-week-old recipient male PDAPP mice (transgenic C57BL/6-ly5.2 (CD45.21) mice that over express mutant human amyloid precursor protein cDNA (hAPPV717F) under the control of the platelet-derived growth factor promoter), which was sublethally irradiated to allow full engraftment of the transplanted hematopoietic stem cells (6 Gy).

Figure 4:
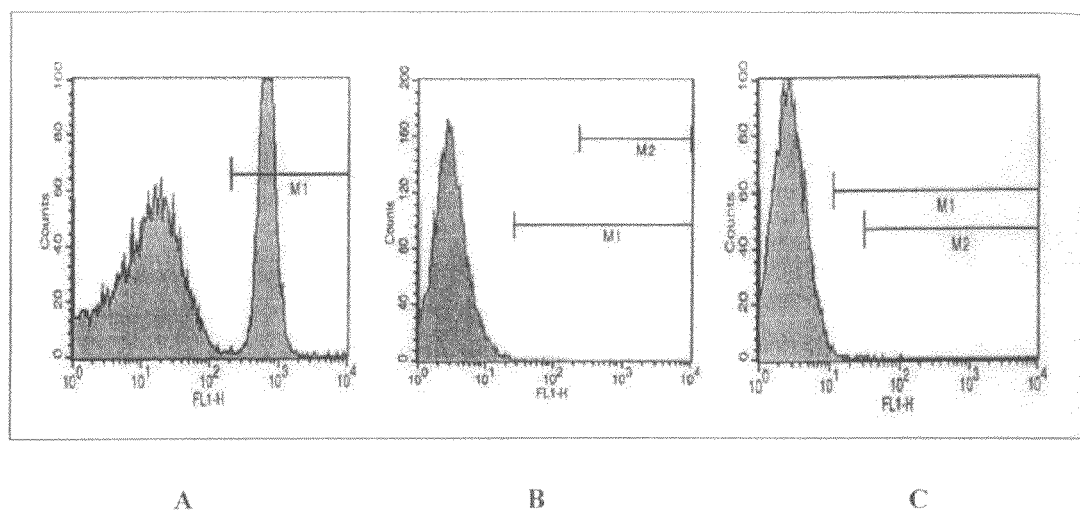
FIG. 4 (A-C) illustrates the flow cytometric analysis of a bone marrow transplanted recipient mouse (CD45.2+) for expression of donor-specific leukocyte common antigen variant CD45.1. Panel A is a histogram of a recipient mouse's white blood cells 30 days after bone marrow transplantation. FITC conjugated anti CD45.1 antibody A20 (PharMingen) was used. Cells in the M1 region are CD45.1$^+$ donor cells and represent about 30% of the total cells. Panel B is a histogram of the same recipient mouse's white blood cells as in the left panel, but without FITC conjugated anti CD45.1 antibody. There are less than 0.1% cells appearing as CD45.1 positive cells, while panel C is a histogram of a recipient mouse without bone marrow transplantation. There are less than 0.1% cells appearing as CD45.1$^+$ cells. This illustrates that bone marrow cells can be transplanted from a donor to a recipient.

As shown in FIG. 4, transplantation of bone marrow cells from a donor mouse expressing the leukocyte common antigen variant CD45.1 into a sublethally irradiated (600 Rads for 3 min) two month old CD45.2 positive recipient mouse generates a chimeric animal in which 30 days after transplantation approximately one third of the circulating hematopoietic cells are derived from the donor as shown by the number of CD45.1 positive cells. The generation of these chimeric mice demonstrates the ability to isolate bone marrow stem cells and to successfully perform bone marrow transplantation in mice. FIG. 4A is a histogram of a recipient mouse's white blood cells 30 days after bone marrow transplantation. FITC conjugated anti CD45.1 antibody A20 (PharMingen) was used. Cells in the M1 region are CD45.1$^+$ donor cells and represent about 30% of the total cells. FIG. 4B is a histogram of the same recipient mouse's white blood cells as in the left panel, but without FITC conjugated anti CD45.1 antibody. There are less than 0.1% cells appearing as CD45.1 positive cells. FIG. 4C is a histogram of a recipient mouse without bone marrow transplantation. There are less than 0.1% cells appearing as CD45.1$^+$ cells.

EXAMPLE 5

Neprilysin Expression on White Blood Cells

As shown in FIG. 5, the NEP-lentivirus are used to transduce bone marrow stem cells from a donor mouse as described in FIG. 4 which are transplanted into a two month old recipient mouse producing neprilysin expression on white blood cells. About 65% of the white blood cells expressed neprilysin prior to transplantation, however since the white blood cells represent ~1% of total blood cells, a relatively small amount of NEP expression is obtained.

Figure 5A:
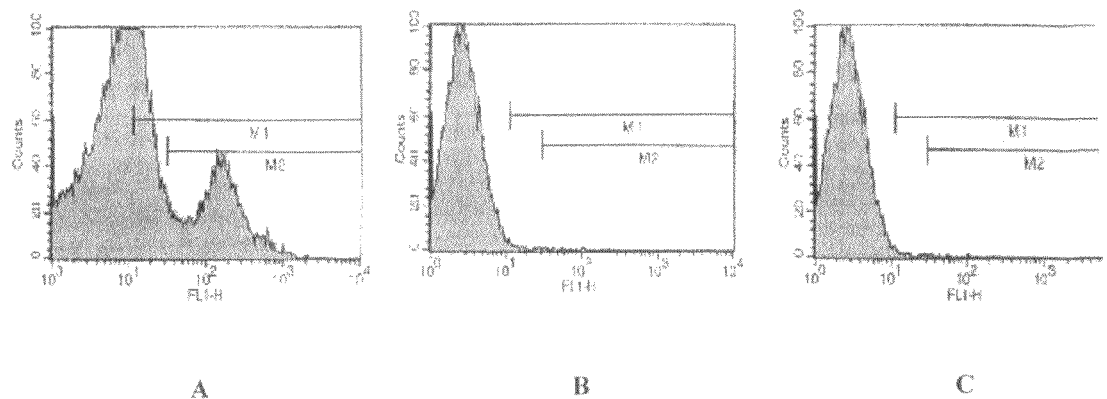
FIG. 5A shows the ability to transplant NEP-lentivirus transduced bone marrow cells from a donor to a recipient mouse: Left—a histogram of lentivirus-NEP-transduced bone marrow stem cells from a donor mouse transplanted to a recipient mouse; Center—a histogram of a recipient mouse without bone marrow transplantation; and Right—a histogram of a recipient mouse after bone marrow transplantation without treatment with FITC conjugated anti-NEP antibody.

FIG. 5A (left) is a histogram of a recipient mouse 30 days after bone marrow transplantation. FITC conjugated anti-NEP antibody CLB-CALLA/1,4F9 (RDI) was used. Cells in the M2 region are neprilysin positive cells and represent about 30% of the total cells. FIG. 5A (middle) is a histogram of a recipient mouse without bone marrow transplantation. There are less than 0.1% cells appearing as neprilysin positive cells. FIG. 5A (right) is a histogram of a recipient mouse after bone marrow transplantation without FITC conjugated anti CLB-CALLA/1,4F9 antibody. There are less than 0.1% cells appearing as CD45.1 positive cells.

Figure 5B:
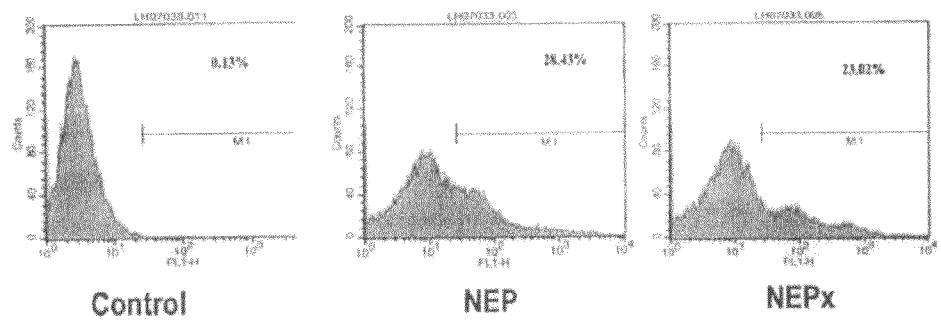
FIGS. 5 (A and B) illustrates the flow cytometric analysis of hematopoietic bone marrow cells from a bone marrow transplant recipient mouse for neprilysin expression (NEP) and inactive neprilyisn (NEPx) compared to an untreated mouse.
Figure 7:
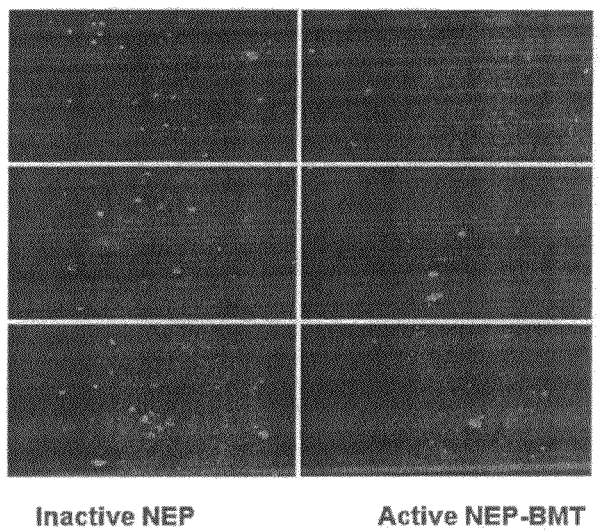
FIG. 7 shows reduced amyloid deposits in the brain of an hAPP transgenic mouse in the brain from NEP peripherally expressed on white blood cells.

FIG. 5B is a repeat and extension of the experiment of FIG. 5A. The NEP-lentivirus was used to transduce bone marrow stem cells from a donor mouse, which were transplanted into a two-month old recipient mouse producing neprilysin expression on white blood cells. About 65% of the bone marrow white blood cells used for transplantation expressed neprilysin. Cells in the M1 region are neprilysin positive cells. Control is a histogram of a recipient mouse without bone marrow transplantation. There are less than 2% cells appearing as neprilysin positive cells. The panel labeled NEP is a histogram of cells from a recipient mouse receiving NEP-lentivirus transduced bone marrow cells and shows greater than 20% of the white blood cells express neprilysin. The panel labeled NEPx is a histogram of cells from a recipient mouse receiving inactive NEP-lentivirus transduced bone marrow cells and shows greater than 20% of the white blood cells express neprilysin.

EXAMPLE 6

ELISA Quantitation of Brain Aβ Peptides

One (1) year after bone marrow transplantation as set forth in Example 4, animals were sacrificed and peripheral blood and brain were harvested. In blood, red blood cells (RBCs, erythrocytes) were analyzed before RBC lysis for white blood cell (WBC, lymphocytes) analyses. FACS analysis was performed for donor cells (CD45.2), NEP expression in different lineages (T cells, B cells, granulocytes, and RBCs), and DNA analysis to determine proviral copy number.

Brains were removed immediately after euthanasia of the mice by $CO_2$ narcosis, frozen in liquid nitrogen, and stored frozen until extraction. Brains were homogenized in 5M guanidine.HCl in 50 mM Tris.HCl. After incubation for 4 h at room temperature, the homogenate was diluted with cold BSAT-DPBS buffer (5% BSA, 0.03% Tween-20 in DPBS) and centrifuged at 16,000×g for 20 min at 4° C. to remove insoluble material. Supernatant fractions were analyzed for $Aβ_{40}$ and $Aβ_{42}$ using isoform-specific ELISA kits (Biosource International, Camarillo, Calif.). As set out in FIG. 6, mice with bone marrow transplantation of white blood cells expressing active NEP showed reduction of Aβ levels in the brain over mice with bone marrow transplantation of white blood cells expressing inactive NEP. Mice with bone marrow transplantation of white blood cells expressing active NEP showed about a 47.5% reduction in $Aβ_{1-40}$ levels in the brain. Mice with bone marrow transplantation of white blood cells expressing active NEP showed about a 30% reduction in $Aβ_{1-42}$ levels in the brain.

EXAMPLE 7

Biotinylation of Neprilysin

Purified neprilysin (1.8 µg) was treated with 2.5 µg of N-hydroxysuccinimde-biotin in a 100 µl reaction containing 100 mM HEPES buffer, pH 8, for the indicated times. An aliquot of 10 µl (0.18 mg) was withdrawn and then subjected to SDS-PAGE, transferred to a PVDF membrane, and then treated with 1/2000 of avidin HRP, and visualized by enhanced chemiluminescense (ECL). Samples at 0, 1 and 2 hrs contained 10 µl of the reaction mixture, while the 4 and 18 hr samples contained 5 µl.

EXAMPLE 8

Biotinylated Neprilysin Retains Activity

Purified neprilysin treated with 2.5 mg of N-hydroxysuccinimde-biotin for the indicated time as in example 7 was assayed for neprilysin activity using glutaryl-Ala-Ala-Phe-MNA (MNA=methoxynaphthylamide) as substrate. As shown in FIG. 10 about 75% of the activity relative to the untreated control was retained after 2 hrs.

EXAMPLE 9

Biotinylation of Isolated Red Blood Cells

Figure 11:
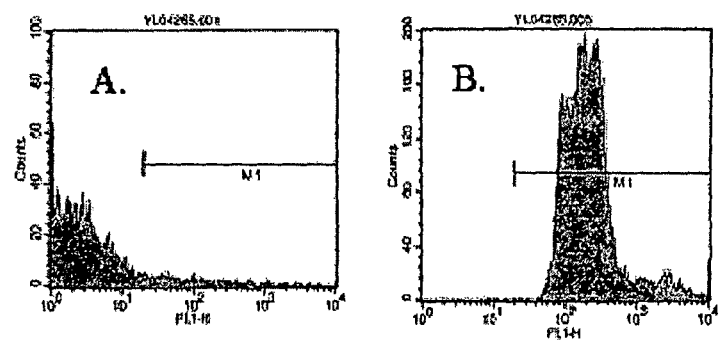
FIG. 11 shows that red blood cells can be biotinylated.

A 10% red blood cell suspension was treated with 75 µM N-hydroxysuccinimde-biotin at room temperature for 2 h in phosphate buffered saline (PBS). After incubation, the red blood cell suspension was washed with PBS containing BSA at 2 mg/ml. FITC-streptavidin was used for FACS analysis. As shown in FIG. 11, Panel A is a control of untreated red blood cells. Panel B shows more than 75% of the red blood cells contained biotin.

EXAMPLE 12

Coupling of Biotinylated Neprilysin to Red Blood Cells

Figure 12:
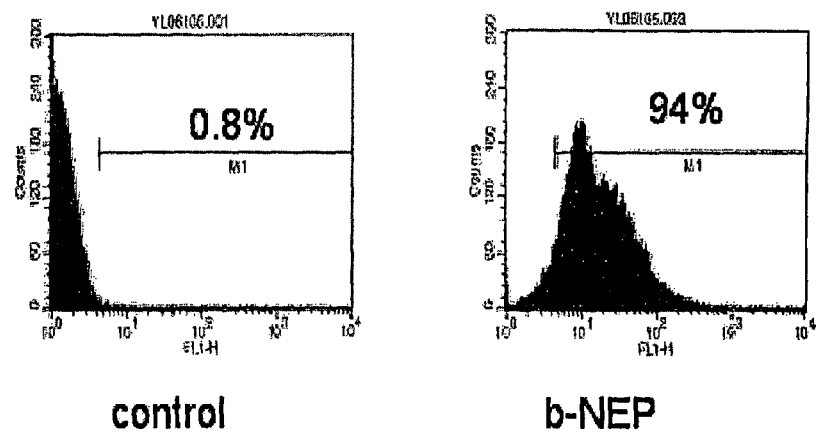
FIG. 12 shows that biotinylated NEP can be linked to biotinylated red blood cells through streptavidin.
Figure 14:
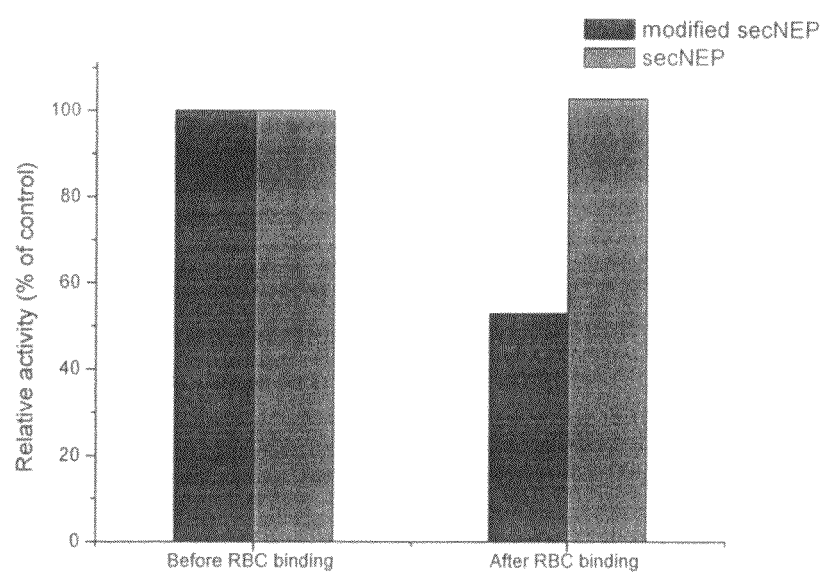
FIG. 14 shows that modified neprilysin containing a C-terminal human red blood cell binding peptide sequence is bound to red blood cells.

Twenty μg of biotinylated neprilysin (b-NEP) was incubated with 5 μl of packed streptavidin-conjugated biotinylated-red blood cells in 100 μl of PBS containing BSA at 2 mg/ml at room temperature for 1 hr. After washing 5 times, the red blood cells were incubated with anti-neprilysin monoclonal antibody labeled with FITC conjugated anti-neprilysin antibody CD10F) at room temperature for half an hour. The sample was then analyzed by FACS. Results in FIG. 12 show that biotinylated neprilysin can be linked to biotinylated red blood cells using streptavidin.

EXAMPLE 13

Modified Neprilysin

Neprilysin was modified with a C-terminal human red blood cell binding peptide sequence linked to the C-terminus of the enzyme. See FIG. 13. The red blood cell binding peptide is derived from a peptide sequence of the histidine rich protein from *P. falciparum* according to the methods provided and incorporated in their entirety by reference herein to Lopez R, Urquiza M, Curtidor H, Eduardo Caminos J, Mora H, Puentes A, Patarroyo M E. *Plasmodium falciparum: red blood cell binding studies of peptides derived from histidine-rich KAHRP-I, HRP-II and HRP-III proteins*. Acta Trop. 2000 May 31; 75(3):349-59.

FIG. 14 shows that modified neprilysin containing a C-terminal human red blood cell binding peptide sequence as shown in example 13 is bound to human red blood cells. The construct shown in FIG. 13 was transiently expressed in HEK cells using a pCSC vector. A cell extract containing the modified NEP was prepared in PBS and incubated with human red blood cells isolated from 1 ml of human blood in 0.2 ml of PBS for 2 hrs at room temperature The sample was then centrifuged and the NEP activity in the supernatant determined with glutaryl-ala-ala-Phe-MNA as substrate. Although none of the unmodified NEP is depleted from the sample by red blood cells, ~50% of the modified NEP is removed by binding to red blood cells.

EXAMPLE 14

Neprilysin Modified to be Bound to an Antibody

FIG. 15. shows a schematic of neprilysin modified with a single chain antibody directed against a red blood cell epitope sequence linked to the C-terminus of the enzyme according to the methods provided and incorporated in their entirety by reference herein to Spitzer D, et al., *ScFv-mediated in vivo targeting of DAF to erythrocytes inhibits lysis by complement*. Mol Immunol. 2004 February; 40(13):911-9. This chimeric protein was shown to bind to mouse red blood cells.

Although illustrative embodiments of the present invention have been described in detail, it is to be understood that the present invention is not limited to those precise embodiments, and that various changes and modifications can be effected therein by one skilled in the art without departing from the scope and spirit of the invention as defined by the appended claims.

What is claimed is:

1. A method for reducing amyloid peptide in the brain of a patient in need thereof, said method comprising:

(a) generating a non-replicating recombinant viral vector comprising a nucleotide sequence encoding neprilysin operably linked to a promoter;

(b) obtaining hematopoietic stem cells from the patient;

(c) introducing the non-replicating recombinant viral vector into the hematopoietic stem cells, ex vivo; and (d) introducing the hematopoietic stem cells of step (c) into the patient via bone marrow transplantation or via intravenous injection, wherein the neprilysin is expressed in the peripheral blood on the surface of one or more of the hematopoietic cells at a sufficient level and duration to result in the efflux of Aβ protein from the brain and facilitate degradation and clearance of Aβ protein from the peripheral blood.

2. The method according to claim 1 wherein the non-replicating recombinant vector is a viral vector selected from the group consisting of adeno-associated virus (AAV) vector, lentivirus, murine leukemia virus and herpes-simplex virus (HSV) vector.

3. The method according to claim 1 wherein the hematopoietic cells are red blood cells, white blood cells, platelets or a combination of all.

4. The method according to claim 3 wherein the hematopoietic cells are red blood cells.

5. The method according to claim 1, wherein said Aβ protein is $A\beta_{1-40}$ or $A\beta_{1-42}$.

* * * * *